US012611179B2

(12) United States Patent
Alkan et al.

(10) Patent No.: US 12,611,179 B2
(45) Date of Patent: Apr. 28, 2026

(54) GUIDED ULTRASOUND IMAGING SYSTEMS

(71) Applicant: Caption Health, Inc., San Mateo, CA (US)

(72) Inventors: Mehmet Eren Alkan, Port Washington, NY (US); Patrick James Brown, Novato, CA (US); Michael G. Cannon, Haverford, PA (US); Nripesh Parajuli, Seattle, WA (US); Tyler Wellman, Fort Collins, CO (US)

(73) Assignee: Caption Health, Inc., Waukesha, WI (US)

( * ) Notice: Subject to any disclaimer, the term of this patent is extended or adjusted under 35 U.S.C. 154(b) by 143 days.

(21) Appl. No.: 18/623,878

(22) Filed: Apr. 1, 2024

(65) Prior Publication Data

US 2025/0302442 A1      Oct. 2, 2025

(51) Int. Cl.
*A61B 8/00* (2006.01)
*A61B 8/08* (2006.01)
*G06V 10/771* (2022.01)

(52) U.S. Cl.
CPC .............. *A61B 8/461* (2013.01); *A61B 8/085* (2013.01); *G06V 10/771* (2022.01); *G06V 2201/031* (2022.01)

(58) Field of Classification Search
CPC .... A61B 8/0461; A61B 8/085; G06V 10/771; G06V 2201/103
See application file for complete search history.

(56) References Cited

U.S. PATENT DOCUMENTS

| | | | |
|---|---|---|---|
| 10,140,710 B2 | 11/2018 | Kreeger | |
| 10,470,677 B2 | 11/2019 | Cadieu et al. | |
| 10,631,791 B2 | 4/2020 | Cadieu et al. | |
| 10,702,242 B2 | 7/2020 | De Jonge et al. | |
| 10,726,548 B2 | 7/2020 | Cadieu et al. | |
| 10,806,402 B2 | 10/2020 | Cadieu et al. | |
| 10,856,848 B2 | 12/2020 | Gafner et al. | |
| 10,937,156 B2 | 3/2021 | Bilenko et al. | |
| 10,993,697 B2 | 5/2021 | Nouri et al. | |
| 11,160,510 B2 | 11/2021 | Cadieu et al. | |
| 11,166,678 B2 | 11/2021 | Cadieu et al. | |
| 11,185,307 B2 | 11/2021 | De Jonge et al. | |
| 11,497,451 B2 | 11/2022 | Cadieu et al. | |
| 11,497,475 B2 | 11/2022 | Cannon et al. | |

(Continued)

FOREIGN PATENT DOCUMENTS

| | | |
|---|---|---|
| CN | 107374674 A | 11/2017 |
| WO | WO-2019075279 A1 | 4/2019 |

(Continued)

OTHER PUBLICATIONS

Ferraz et al., Assisted probe guidance in cardiac ultrasound: A review. Front Cardiovasc Med. 10: 1056055, pp. 1-9 (2023).

(Continued)

*Primary Examiner* — Chao Sheng
(74) *Attorney, Agent, or Firm* — SPQ IP LLC

(57)       ABSTRACT

Disclosed herein are ultrasound imaging systems which provide automatic assessment of B-lines in ultrasound images of a lung of a subject, which can be used, for example, to assist in acquisition of diagnostic images for assessing a health condition of a lung of a subject.

17 Claims, 10 Drawing Sheets

(56)  References Cited

U.S. PATENT DOCUMENTS

| | | | |
|---|---|---|---|
| 11,540,808 B2 | 1/2023 | Nouri et al. | |
| 11,564,657 B2 | 1/2023 | De Jonge et al. | |
| 11,670,077 B2 | 6/2023 | Gafner et al. | |
| 2015/0214434 A1 | 7/2015 | Fujiwara et al. | |
| 2017/0360402 A1* | 12/2017 | de Jonge | A61B 8/5207 |
| 2018/0153505 A1 | 6/2018 | Cadieu et al. | |
| 2019/0105013 A1* | 4/2019 | Wang | A61B 8/463 |
| 2020/0245970 A1 | 8/2020 | Cadieu et al. | |
| 2020/0245976 A1 | 8/2020 | Cadieu et al. | |
| 2021/0052253 A1 | 2/2021 | Cadieu et al. | |
| 2021/0161508 A1* | 6/2021 | Schadewaldt | A61B 8/0883 |
| 2021/0236094 A1 | 8/2021 | Cannon et al. | |
| 2022/0104790 A1 | 4/2022 | Cadieu et al. | |
| 2022/0167945 A1 | 6/2022 | De Jonge et al. | |
| 2022/0233167 A1 | 7/2022 | Harker et al. | |
| 2023/0117915 A1 | 4/2023 | Nouri et al. | |

FOREIGN PATENT DOCUMENTS

| | | |
|---|---|---|
| WO | WO-2021034981 A1 | 2/2021 |
| WO | WO-2022241155 A1 | 11/2022 |

OTHER PUBLICATIONS

Gargani et al., How I do it: Lung ultrasound. Cardiovascular Ultrasound. 12:25, pp. 1-10 (2014).

Li et al., Autonomous navigation of an ultrasound probe towards standard scan planes with deep reinforcement learning. IEEE International Conference on Robotics and Automation. arXiv:2103.00718 [cs.RO], pp. 1-7 (2021). Available at https://arxiv.org/abs/2103.00718.

Pasdeloup et al., Real-time echocardiography guidance for optimized apical standard views. Ultrasound Med Biol. 49(1):333-346 (2023).

\* cited by examiner

Acquire ultrasound images of a subject — 101

Detect imaging landmarks — 102

103 — Provide probe guidance instructions based on detected landmarks

GUIDED ULTRASOUND IMAGING SYSTEMS

BACKGROUND

Ultrasound imaging is a non-invasive diagnostic modality that does not use ionizing radiation, provides a wide range of medical applications, images tissue and blood flow, provides exhaustive clinical measurements, and is affordable and portable. Unlike many other imaging methods however, ultrasound often requires extensive training of the person operating the device and acquiring the images. The correct methods to apply the ultrasound transducer to the patient are complex and challenging to learn, which limits the reach of ultrasound in patient care. Machine learning systems can provide navigation instructions in some cases, to guide untrained users to proper transducer placement, however, use of guided ultrasound imaging systems and devices by non-expert users is often limited to organs which are rich in observable features. Moreover, guided probe navigation can be challenging even in cases where target organs are feature rich if the user's probe placement is so far off that it is unable to sufficiently visualize the organ. Accordingly, described herein are methods and systems which can assist in both the acquisition and interpretation of ultrasound images, and provide probe guidance for target organs which have limited visualizable features and/or where target organs are not sufficiently within view of an acquired image by utilizing detectable features of adjacent organs.

SUMMARY

In some aspects, described herein are ultrasound imaging systems configured for conducting a diagnostic procedure on a subject. In some aspects, the systems comprise an ultrasound imaging probe. In some aspects, the systems comprise a computing system. In some aspects, the systems comprise a computer-readable storage medium, storing instructions that, when executed by a processor of the computing system cause the ultrasound imaging system to perform any of the methods described herein.

In some aspects, the systems are configured to receive a selection of the diagnostic procedure for imaging a target organ of the subject. In some aspects, the systems are configured to acquire a plurality of ultrasound images comprising one or more features of an imaged organ of the subject using the ultrasound imaging probe. In some aspects, the systems are configured to process the plurality of ultrasound images using a machine learning model to automatically determine that the one or more features of the imaged organ comprise features corresponding to features of an adjacent organ of the subject. In some aspects, the systems are configured to determine based at least in part on the features corresponding to the adjacent organ, one or more probe placement instructions expected to produce an improvement in a quality of a subsequently acquired ultrasound image of the target organ. In some aspects, the systems are configured to provide a user of the ultrasound imaging system with the one or more probe placement instructions.

In some aspects, described herein are methods for guiding an ultrasound imaging procedure. In some aspects, the methods comprise selecting a diagnostic procedure for imaging a target organ of a subject using an ultrasound imaging probe of an ultrasound imaging system. In some aspects, the methods comprise acquiring a plurality of ultrasound images comprising one or more features of an imaged organ of the subject using the ultrasound imaging probe. In some aspects, the methods comprise processing the plurality of ultrasound images using a machine learning model to automatically determine that the one or more features of the imaged organ comprise features corresponding to features of an adjacent organ of the subject. In some aspects, the methods comprise computing based at least in part on the features corresponding to the adjacent organ, one or more probe placement instructions expected to produce an improvement in a quality of a subsequently acquired ultrasound image of the target organ. In some aspects, the methods comprise providing a user of the ultrasound imaging system with the one or more probe placement instructions.

In some aspects, the imaged organ is the lung of the subject and the target organ is the heart of the subject. In some aspects, the imaged organ is the diaphragm of the subject and the second organ is the lung of the subject. In some aspects, the diagnostic procedure comprises a lung imaging procedure. In some aspects, the one or more probe placement instructions comprise instructions to adjust a landing spot of the ultrasound imaging probe.

In some aspects, the system is further configured to automatically identify one or more lung zones from comprised in the acquired plurality of ultrasound images. In some aspects, the automatic identification comprises an identification that a visible lung zone of the one or more lung zones comprised in the acquired plurality of ultrasound images is different from a target lung zone of the diagnostic procedure.

In some aspects, the one or more probe placement instructions comprise instructions to adjust the ultrasound imaging probe to a probe placement expected to produce subsequent images of the target lung zone of the diagnostic procedure. In some aspects, the one or more probe placement instructions comprise instructions to slide the ultrasound imaging probe in a direction expected to point a transducer of the probe toward the target lung zone of the diagnostic procedure.

In some aspects, providing the one or more probe placement instructions comprises determining that a plurality of imaging landmarks are present in the plurality of acquired ultrasound images; and computing the one or more probe placement instructions based at least in part on the plurality of imaging landmarks. In some aspects, the system is configured to identify that one or more of the plurality of imaging landmarks correspond to features that are not comprised in the target organ.

In some aspects, the plurality of imaging landmarks comprise anatomical landmarks of the target organ and/or anatomical landmarks of the adjacent organ. In some aspects, the plurality of imaging landmarks comprises: lung imaging landmarks selected from the group of: pleural lines, A-lines, B-lines and rib shadows; or cardiac imaging landmarks selected from the group of: a parasternal long axis view, a parasternal short axis view, an apical two, three, four or five chamber view, and a subcostal view. In some aspects, the diagnostic procedure comprises a sequential evaluation of a plurality of organs. In some aspects, the plurality of organs comprise a heart of the subject and one or more lungs of the subject.

In some aspects, the system is further configured to acquire a subsequent plurality of ultrasound images of the target organ, and identify a subset of the subsequently acquired plurality of ultrasound images which meet a minimum quality threshold and/or minimum length threshold; and automatically saving the subset of the subsequently acquired ultrasound images in a memory of the ultrasound imaging system. In some aspects, one or more of the plurality of imaging landmarks is annotated and displayed to a user.

In some aspects, the one or more probe placement instructions comprise a plurality of probe placement instructions and are displayed to a user through a graphical user interface of the ultrasound system. In an aspect, described herein are non-transitory computer-readable media, storing instructions that, when executed by a processor of a computer, cause the computer to perform any of the methods described herein.

In one aspect, described herein are ultrasound imaging systems configured for conducting a diagnostic procedure on a subject. In some aspects, the systems comprise an ultrasound imaging probe. In some aspects, the systems comprise a computing system. In some aspects, the systems comprise a computer-readable storage medium, storing instructions that, when executed by a processor of the computing system cause the ultrasound imaging system to perform any of the methods described herein.

In some aspects, the systems are configured to obtain a plurality of ultrasound images of at least a portion of a lung of a subject. In some aspects, the systems are configured to process the plurality of ultrasound images to automatically classify two or more features selected from the group of: A-lines, B-lines, pleural lines, and rib shadows comprised within the acquired plurality of ultrasound images. In some aspects, the systems are configured to automatically assess a clinical quality of the plurality of ultrasound images based on the two or more automatically classified features. In some aspects, the systems are configured to output an indication of the assessed clinical quality to a user.

In another aspect described herein, are methods for ultrasound imaging. In some aspects, the methods comprise obtaining a plurality of ultrasound images of at least a portion of a lung of a subject. In some aspects, the methods comprise processing the plurality of ultrasound images to automatically classify two or more features selected from the group of: A-lines, B-lines, pleural lines, and rib shadows comprised within the acquired plurality of ultrasound images. In some aspects, the methods comprise automatically assessing a clinical quality of the plurality of ultrasound images based on the two or more automatically classified features. In some aspects, the methods comprise outputting an indication of the assessed clinical quality to a user.

In another aspect, described herein are non-transitory computer-readable medium, storing instructions that, when executed by a processor of a computer, cause the computer to perform any of the methods described herein. In some aspects, systems described herein are configured to obtain a plurality of ultrasound images of at least a portion of a lung of a subject.

In some aspects, systems described herein are configured to process the plurality of ultrasound images to automatically classify B lines in the acquired plurality of ultrasound images. In some aspects, systems described herein are configured to distinguish B-lines comprised within the plurality of ultrasound images from one or more alternate features comprised within the plurality of ultrasound images to obtain featurized B-lines associated with the acquired plurality of ultrasound images. In some aspects, systems described herein are configured to estimate a rib space of the subject based on the acquired plurality of ultrasound images. In some aspects, systems described herein are configured to automatically determine, based at least in part on the featurized B-lines and the estimated rib space, one or more B-line classifiers. In some aspects, systems described herein are configured to output the one or more B-line classifiers to a user of the ultrasound imaging system.

In some instances, methods described herein comprise obtaining a plurality of ultrasound images of at least a portion of a lung of a subject. In some aspects, methods described herein comprise processing the plurality of ultrasound images to automatically classify B lines in the acquired plurality of ultrasound images. In some aspects, methods described herein comprise distinguishing B-lines comprised within the plurality of ultrasound images base at least in part on one or more alternate features comprised within the plurality of ultrasound images to obtain featurized B-lines associated with the acquired plurality of ultrasound images. In some aspects, methods described herein comprise estimating a rib space of the subject based on the acquired plurality of ultrasound images. In some aspects, methods described herein comprise automatically determining, based at least in part on the featurized B-lines and the estimated rib space, one or more B-line classifiers In some aspects, methods described herein comprise outputting the one or more B-line classifiers to a user.

In some aspects, the plurality of ultrasound images is classified based on three or more features selected from the group of A-lines, B-lines, pleural lines, and rib shadows comprised within the acquired plurality of ultrasound images. In some aspects, the plurality of ultrasound images is classified based on each of the of A-lines, B-lines, pleural lines, or rib shadows present within the acquired plurality of ultrasound images. In some aspects, the methods or systems further comprise selecting a diagnostic procedure and acquiring the plurality of ultrasound images, wherein the assessed clinical quality comprises an assessment of the suitability of the acquired images for the selected diagnostic procedure.

In some aspects, the methods or systems further comprise determining based on the assessed clinical quality whether the obtained images comprise images of a normal lung or an abnormal lung; and providing the user with an indication of whether one or more of the obtained images are of a normal lung or an abnormal lung. In some aspects, the methods or systems further comprise assessing an overall clinical quality of an image clip comprising the plurality of images and automatically saving the image clip in a memory of the ultrasound imaging system based on detection that the overall quality of the image clip is at least a threshold quality and a length of the image clip is at least a threshold length.

In some aspects, the image clip length threshold and the image clip quality threshold are a minimum length and minimum quality that are clinically acceptable for completion of the selected diagnostic procedure. In some aspects, minimum image clip length comprises at least a full respiration cycle. In some aspects, the image clip is assessed in real time, during performance of the diagnostic procedure.

In some aspects, the methods or systems further comprise automatically detecting that a different mode of respiration would improve the clinical quality of a subsequently acquired plurality of ultrasound images; and instructing the user to have the patient perform the different respiratory mode during the diagnostic procedure. In some aspects, the different mode of respiration comprises a full exhalation while preventing an inhalation, a full inhalation while preventing an exhalation, a full exhalation with a partial exhalation while inhibiting further inhalation or exhalation, a partial inhalation while inhibiting further inhalation or exhalation, or a full inhalation.

In some aspects, the methods or systems further comprise alerting the user to an absence from one or more of the plurality of images of one or more landmark features, the one or more landmark features comprising a pleural line and/or a rib shadow. In some aspects, the indication is provided in real time during a diagnostic procedure and the processing comprises providing the plurality of ultrasound images as input to a machine learning model.

In some aspects, the assessment comprises: automatically determining which lung zone is being scanned and/or the assessment of the clinical quality is based at least in part on the lung zone being imaged. In some aspects, the lung zone being imaged is a lower lung zone, and the assessment is based at least in part on a presence, absence, or visibility of one or more alternate organs or alternate features comprised in the plurality of images.

In some aspects, the one or more alternate organs or features comprise a spleen, a liver, a kidney, a spine, a curtain sign, and/or combinations thereof. In some aspects, the machine learning model is trained with training data comprising one or more images annotated with information about rib spacing, A-lines, B-lines, rib shadows, respiratory mode, clinical quality, and/or combinations thereof. In some aspects, the machine learning model is trained with training data comprising one or more images annotated with information about a health status of a lung the training image.

In some aspects, the one or more B-line classifiers are provided based at least in part on a detection of one or more pleural lines, and/or based at least in part on a detection of one or more normal A-lines. In some aspects, the plurality of ultrasound images are comprised in an image clip, and the one or more B-line classifiers are determined for each image of the image clip.

In some aspects, the methods or systems further comprise assigning a B-line score to the image clip based on the one or more B-line classifiers. In some aspects, the one or more B-line classifiers comprise a B-line count, and the B-line score assigned to the image clip comprises a total number of detected B-lines. In some aspects, the method further comprises highlighting the detected B-lines and/or the estimated rib space within one or more of the plurality of ultrasound images.

In some aspects, the methods or systems further comprise determining that the assigned B-line score meets a threshold and automatically saving the image clip in a memory of an ultrasound system. In some aspects, the methods or systems further comprise identifying a subset of the plurality of images comprised in the image clip which are representative of the clip; and displaying one or more images of the representative subset by a display.

In some aspects, the alternate features comprise: A-lines, pleural lines, or rib shadows. In some aspects, B-lines are distinguished from A-lines, pleural lines, and rib shadows. In some aspects, the method further comprises annotating the alternate features in one or more of the plurality of ultrasound images. In some aspects, each B-line, A-line, pleural line, and rib shadow present in the plurality of ultrasound images is annotated and displayed to a user. In some aspects, the annotation and display is performed in real time during acquisition of the ultrasound images. In some aspects, the annotation and display is performed offline using a previously acquired ultrasound image clip.

In some aspects, the distinguishing is performed by submitting the plurality of ultrasound images to a trained machine learning model. In some aspects, the trained machine learning model comprises one or more neural network. In some aspects, the methods or systems further comprise classifying a pathology of the subject based on the one or more B-line classifiers. In some aspects, the pathology is lung deaeration, and the method further comprises alerting a user to a severity of the lung deaeration.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative aspects of the present disclosure are shown and described. As will be realized, the present disclosure is capable of other and different aspects, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative aspects, in which the principles of the invention are utilized, and the accompanying drawings (also "Figure" and "FIG." herein), of which:

DETAILED DESCRIPTION

While various aspects of the invention have been shown and described herein, it will be obvious to those skilled in the art that such aspects are provided by way of example only. Numerous variations, changes, and substitutions may occur to those skilled in the art without departing from the invention. It should be understood that various alternatives to the aspects of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain inventive aspects herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Where particular values are described in the application and claims, unless otherwise stated the term "about" meaning within an acceptable error range for the particular value may be assumed.

Figure 1:
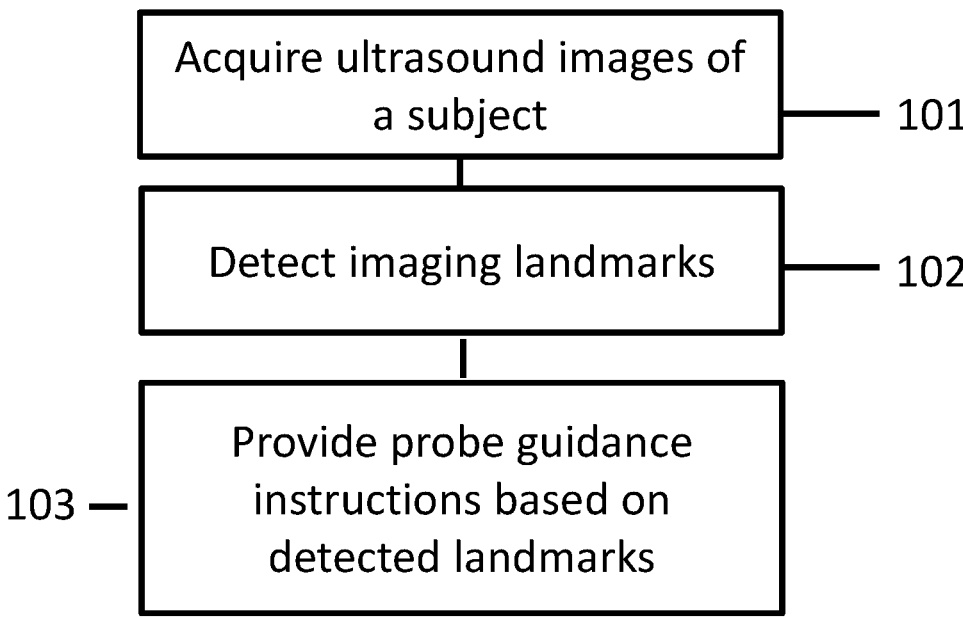
FIG. 1 illustrates an example workflow for guiding an ultrasound imaging procedure according to aspects described herein.

Methods and systems described herein can be implemented according to numerous alternative workflows. For example, the workflow illustrated in FIG. 1 comprises: acquiring ultrasound images a subject 101, for example, using an imaging probe of an ultrasound imaging system (e.g. using a transducer of a two-dimensional ultrasound imaging system such as a linear probe, a curvilinear probe, or a phased array probe), detecting imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) 102, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.). Guidance instructions are then provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 103.

Figure 2:
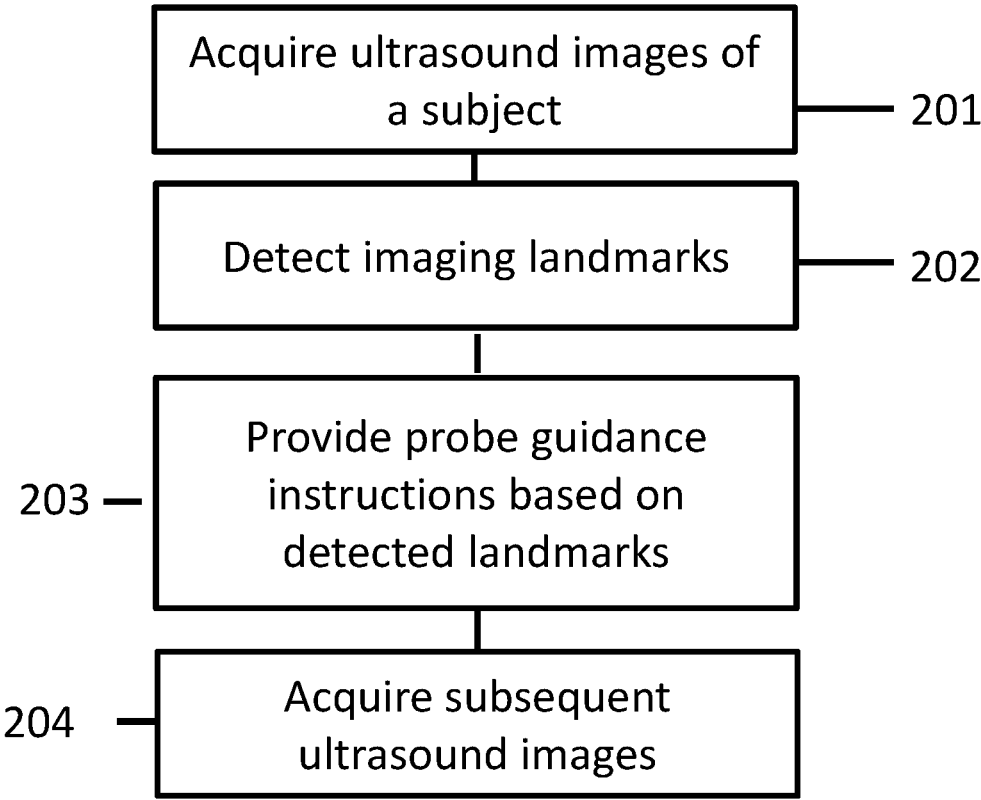
FIG. 2 illustrates an alternate example workflow for guiding an ultrasound imaging procedure according to aspects described herein.

An alternate example workflow, illustrated in FIG. 2 comprises: acquiring ultrasound images a subject 201, for example, using an imaging probe of an ultrasound imaging system (e.g. using a transducer of a two-dimensional ultrasound imaging system such as a linear probe, a curvilinear probe, or a phased array probe), detecting imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) 202, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.). Guidance instructions are then provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 203; and subsequent images that are improved (for example, in terms of diagnostic quality and/or feature visualization) are acquired after the user has repositioned the imaging probe 204.

Figure 3:
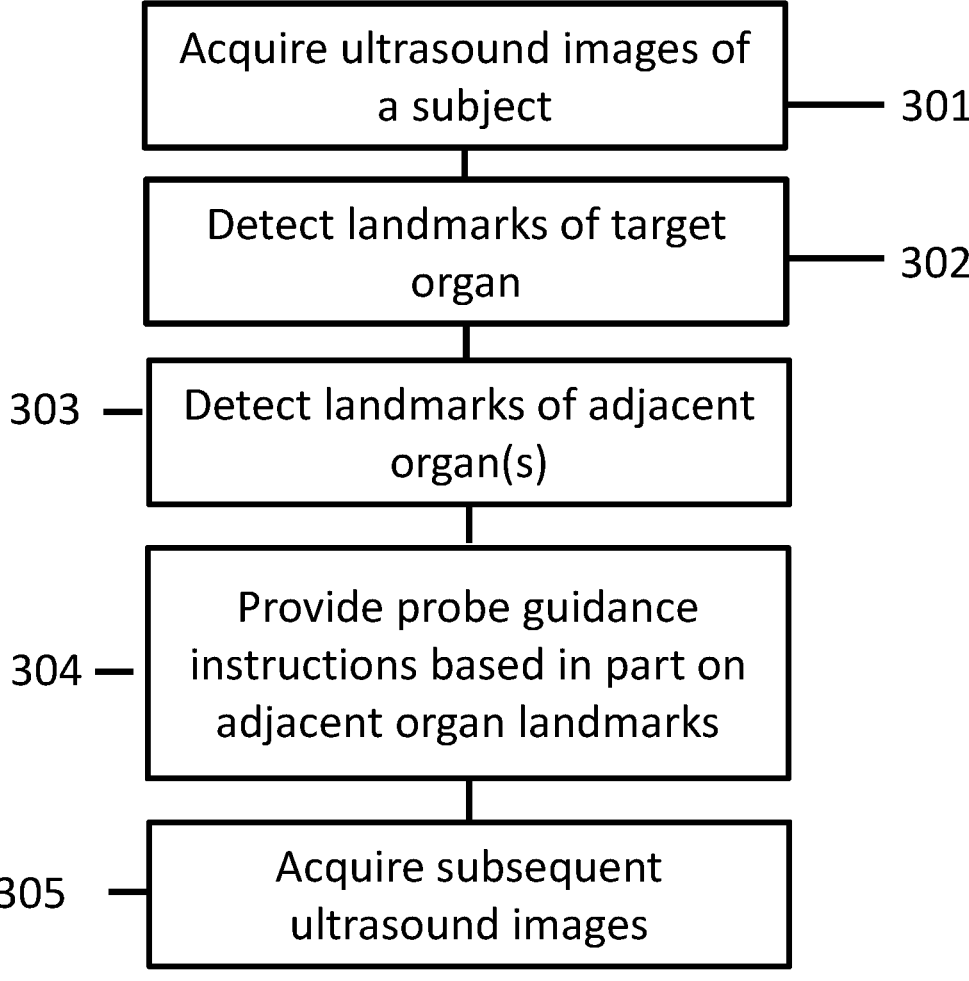
FIG. 3 illustrates an example workflow for guiding an ultrasound imaging procedure based on landmarks of a target organ and/or an adjacent organ according to aspects described herein.

An alternate example workflow, illustrated in FIG. 3 comprises: acquiring ultrasound images a subject 301, for example, using an imaging probe of an ultrasound imaging system (e.g. using a transducer of a two-dimensional ultrasound imaging system such as a linear probe, a curvilinear probe, or a phased array probe), detecting imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) of a target organ 302, and one or more adjacent organs (such as an alternate lung, a diaphragm, a rib shadow, or a cardiac landmark when the target organ is a lung, or lung or bone features when the target organ is a heart) 303, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.). Guidance instructions are then provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 304; and subsequent images that are improved (for example, in terms of diagnostic quality and/or feature visualization) are acquired after the user has repositioned the imaging probe 305.

Figure 4:
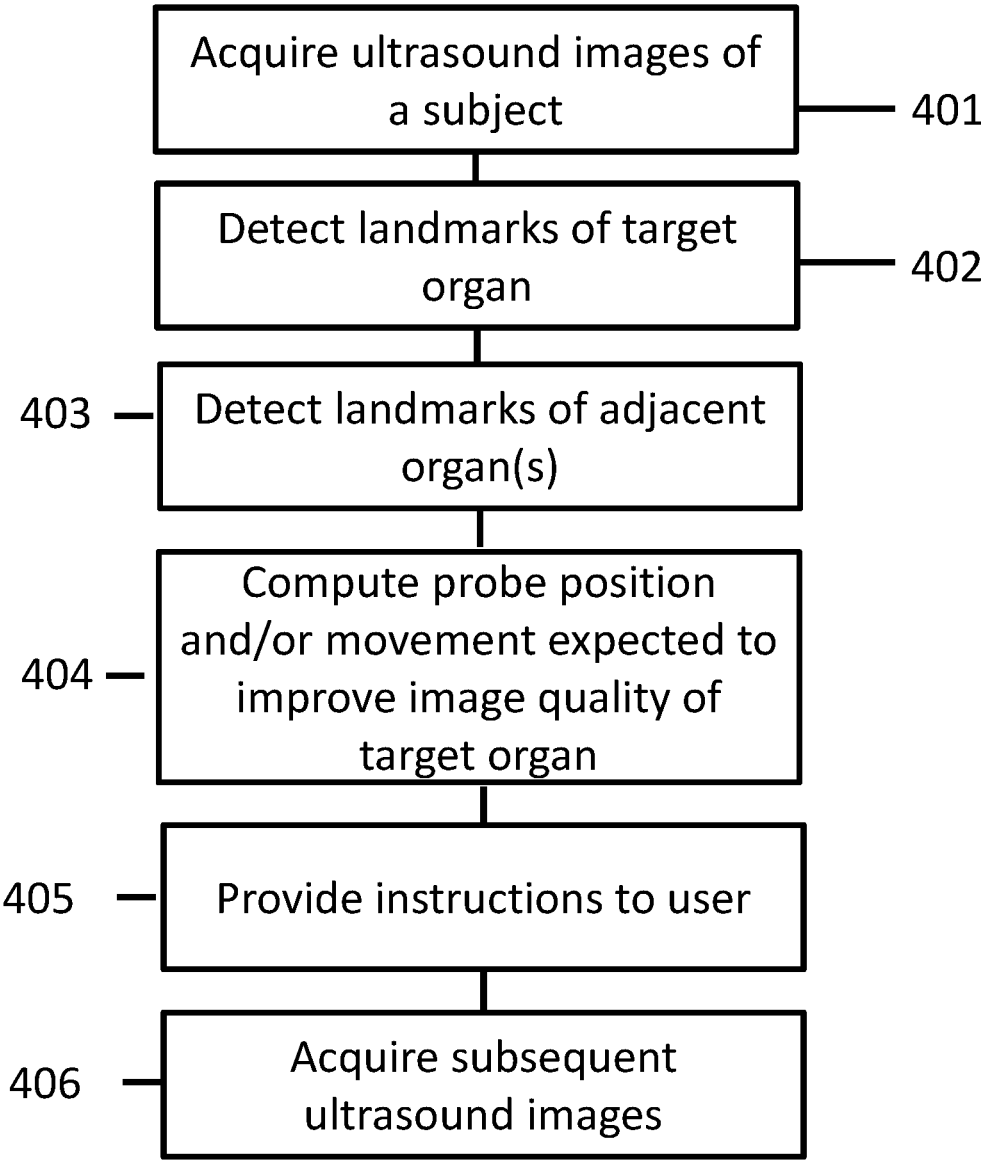
FIG. 4 illustrates an further example workflow for guiding an ultrasound imaging procedure based on landmarks of a target organ and/or an adjacent organ according to aspects described herein.

Another alternate example workflow, illustrated in FIG. 4 comprises: acquiring ultrasound images a subject 401, for example, using an imaging probe of an ultrasound imaging system (e.g. using a transducer of a two-dimensional ultrasound imaging system such as a linear probe, a curvilinear probe, or a phased array probe), detecting imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) of a target organ 402, and one or more adjacent organs (such as an alternate lung, a diaphragm, a rib shadow, or a cardiac landmark when the target organ is a lung, or lung or bone features when the target organ is a heart) 403, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.) or using any of the featurization methods described herein. A contemporaneous probe position, an ideal probe position, and/or a deviation between, or one or more movements (such as any of the movements described further herein) are computed based on the detected imaging landmarks 404, and guidance instructions are provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 405; and subsequent images that are improved (for example, in terms of diagnostic quality and/or feature visualization) are acquired after the user has repositioned the imaging probe 406.

Figure 5:
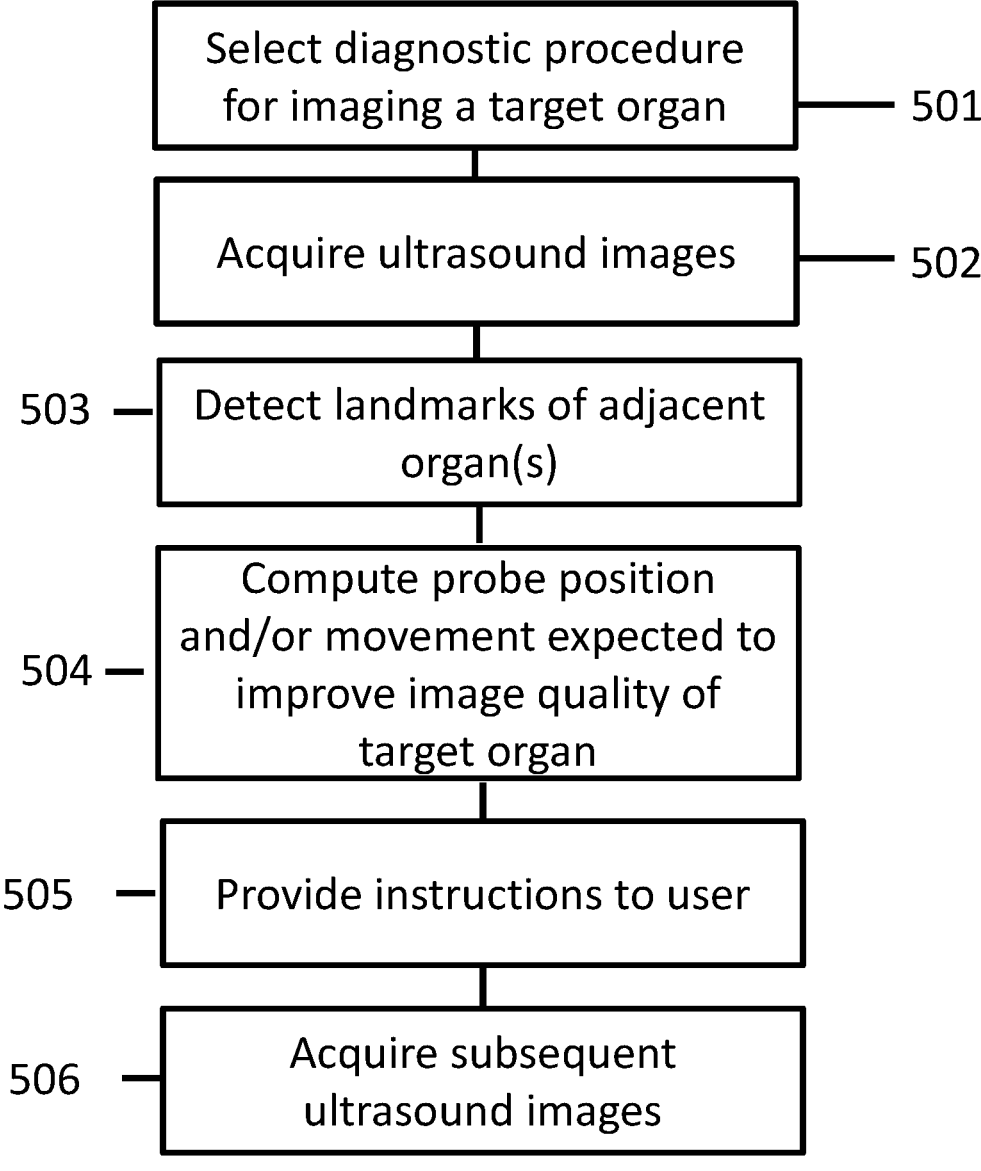
FIG. 5 illustrates an illustrates an example workflow for guiding a diagnostic procedure based on landmarks of a target organ and/or an adjacent organ according to aspects described herein.

Another alternate example workflow, illustrated in FIG. 5 comprises: selecting a diagnostic procedure, for example, a lung imaging procedure for diagnosing abnormal lung aeration or a cardiac imaging procedure for evaluation of valve function, ejection fraction, and/or classification of a pathology 501, acquiring ultrasound images a subject 502, for example, using an imaging probe of an ultrasound imaging system (e.g. using a transducer of a two-dimensional ultrasound imaging system such as a linear probe, a curvilinear probe, or a phased array probe), detecting imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) of a target organ and/or one or more adjacent organs (such as an alternate lung, a diaphragm, a rib shadow, or a cardiac landmark when the target organ is a lung, or lung or bone features when the target organ is a heart) 503, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.) or using any of the featurization methods described herein. A contemporaneous probe position, an ideal probe position, and/or a deviation between, or one or more movements (such as any of the movements described further herein) are computed based on the detected imaging landmarks 504, and guidance instructions are provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 505; and subsequent images that are improved (for example, in terms of diagnostic quality and/or feature visualization) are acquired after the user has repositioned the imaging probe 506.

Figure 6:
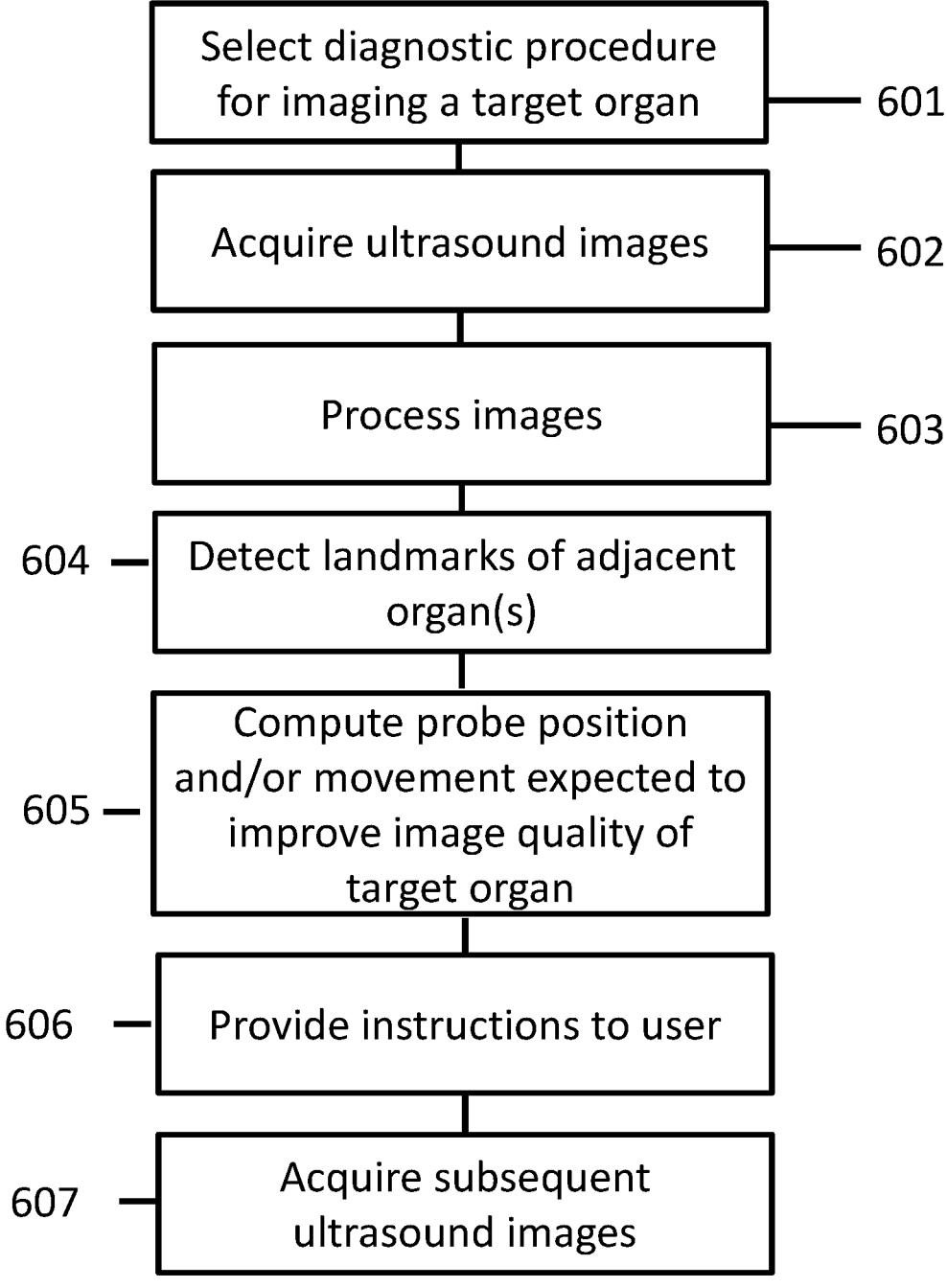
FIG. 6 illustrates a further example workflow for guiding an ultrasound imaging procedure based according to aspects described herein.

Another alternate example workflow, illustrated in FIG. 6 comprises: selecting a diagnostic procedure, for example, a lung imaging procedure for diagnosing abnormal lung aeration or a cardiac imaging procedure for evaluation of valve function, ejection fraction, and/or classification of a pathology 601, acquiring ultrasound images a subject 602, for example, using an imaging probe of an ultrasound imaging system (e.g. using a transducer of a two-dimensional ultrasound imaging system such as a linear probe, a curvilinear probe, or a phased array probe), processing images, for example by using any of the methods described herein to detect or identify image features 603, imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) of a target organ and/or one or more adjacent organs (such as an alternate lung, a diaphragm, a rib shadow, or a cardiac landmark when the target organ is a lung, or lung or bone features when the target organ is a heart) 604, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.) or using any of the featurization methods described herein. A contemporaneous probe position, an ideal probe position, and/or a deviation between, or one or more movements (such as any of the movements described further herein) are computed based on the detected imaging landmarks 605, and guidance instructions are provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 606; and subsequent images that are improved (for example, in terms of diagnostic quality and/or feature visualization) are acquired after the user has repositioned the imaging probe 607.

Figure 7:
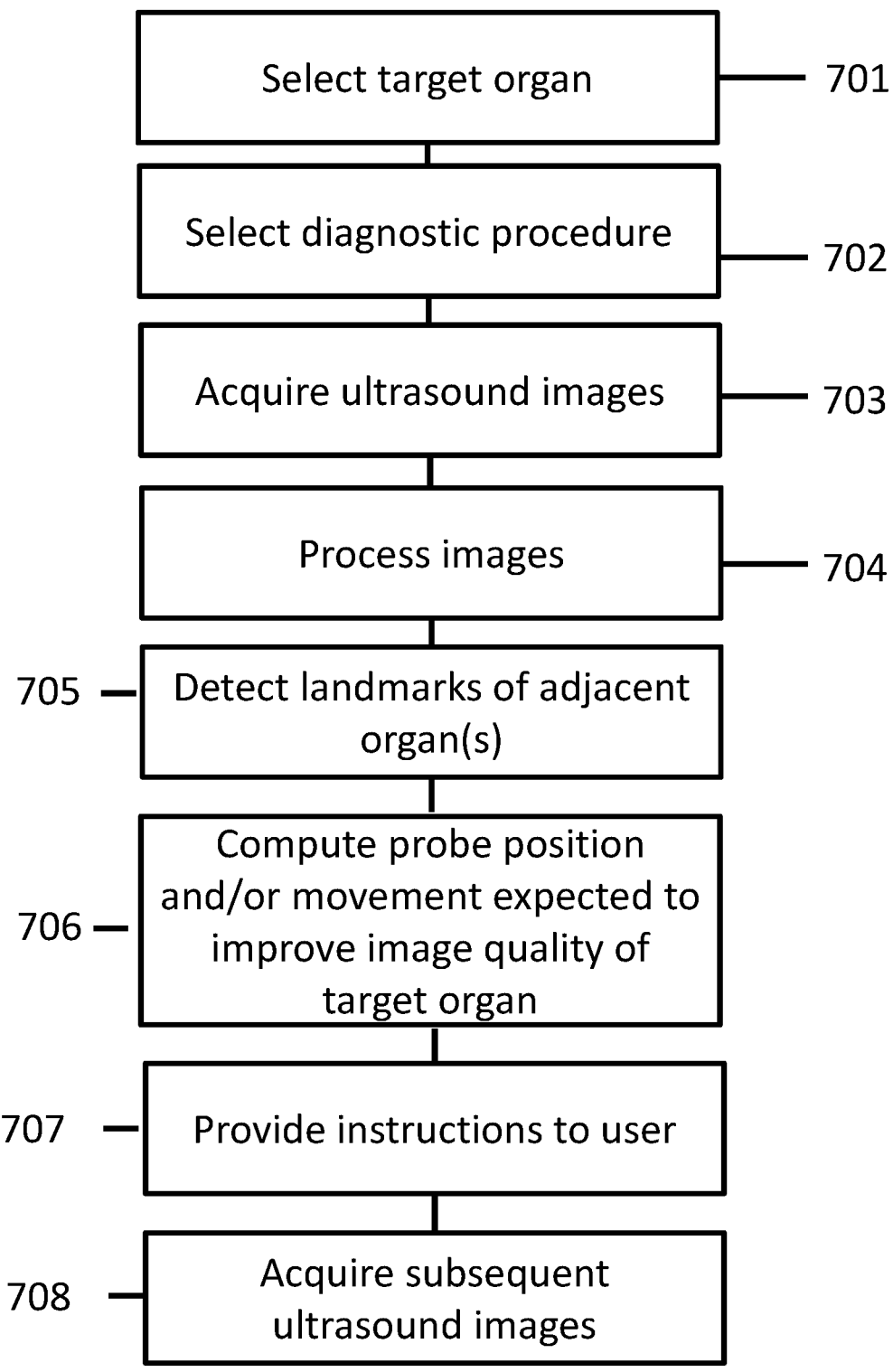
FIG. 7 illustrates a further example workflow for guiding an ultrasound imaging procedure based according to aspects described herein.

Another alternate example workflow, illustrated in FIG. 7 comprises: selecting a target organ of a subject, for example, a left lung, a right lung, a heart, a liver, or a spleen 701; selecting a diagnostic procedure, for example, a lung imaging procedure for diagnosing abnormal lung aeration or a cardiac imaging procedure for evaluation of valve function, ejection fraction, and/or classification of a pathology 702, acquiring ultrasound images a subject 703, for example, using an imaging probe of an ultrasound imaging system (e.g. using a transducer of a two-dimensional ultrasound imaging system such as a linear probe, a curvilinear probe, or a phased array probe), processing images, for example by using any of the methods described herein to detect or identify image features 704, imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) of a target organ and/or one or more adjacent organs (such as an alternate lung, a diaphragm, a rib shadow, or a cardiac landmark when the target organ is a lung, or lung or bone features when the target organ is a heart) 705, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.) or using any of the featurization methods described herein. A contemporaneous probe position, an ideal probe position, and/or a deviation between, or one or more movements (such as any of the movements described further herein) are computed based on the detected imaging landmarks 706, and guidance instructions are provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 707; and subsequent images that are improved (for example, in terms of diagnostic quality and/or feature visualization) are acquired after the user has repositioned the imaging probe 708.

Figure 8:
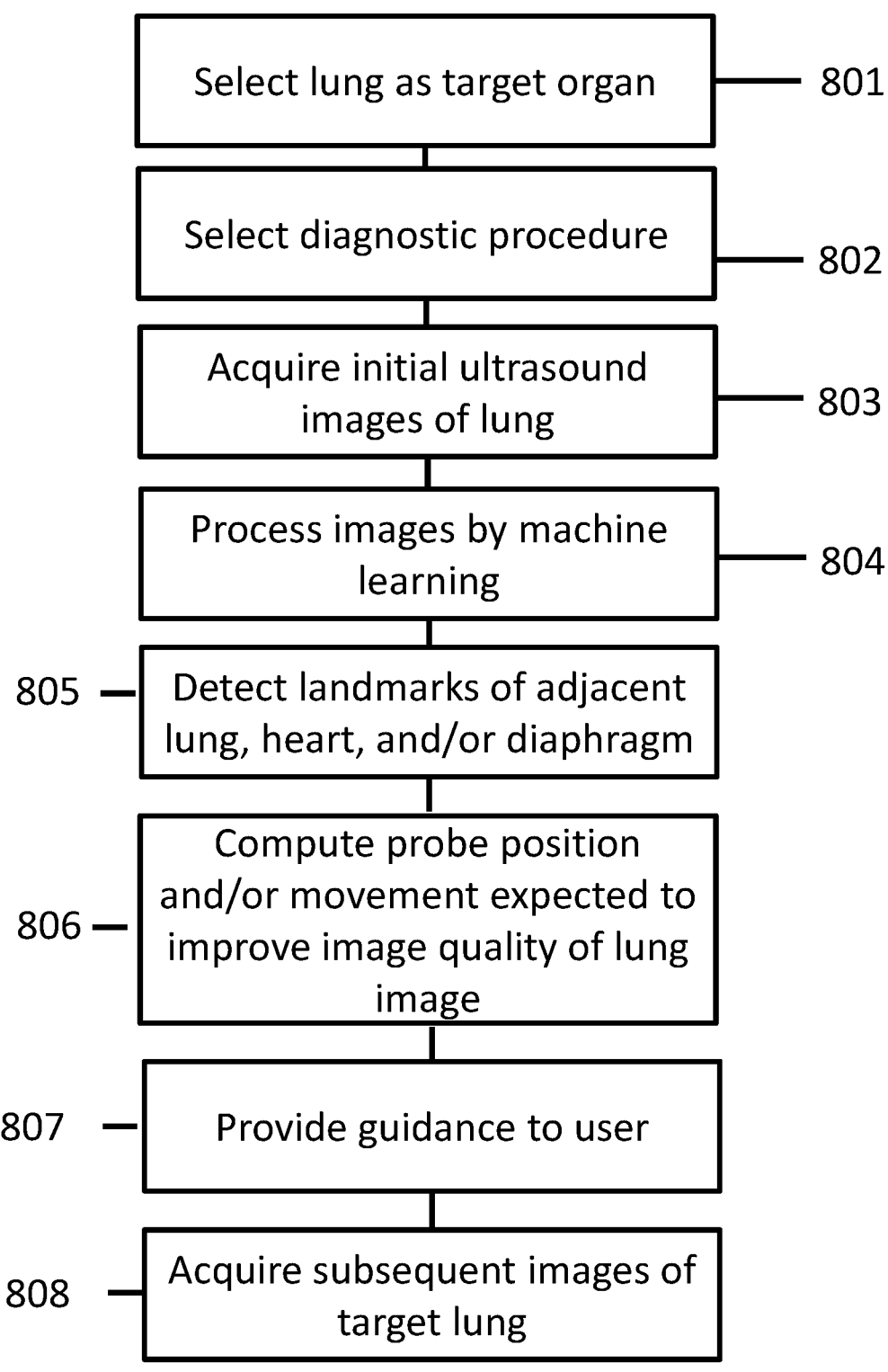
FIG. 8 illustrates a further example workflow for guiding an ultrasound imaging procedure based according to aspects described herein.

Another alternate example workflow, illustrated in FIG. 8 comprises: selecting a lung of a subject as a target organ 801; selecting a diagnostic procedure, for example, a lung imaging procedure for diagnosing abnormal lung aeration or lung function 802, acquiring ultrasound images a subject 803, for example, using an imaging probe of an ultrasound imaging system (e.g. using a transducer of a two-dimensional ultrasound imaging system such as a linear probe, a curvilinear probe, or a phased array probe), processing images, for example by using any of the methods described herein to detect or identify image features 804, imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) of a target organ and/or one or more adjacent organs (such as an alternate lung, a diaphragm, a rib shadow, or a cardiac landmark) 805, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, etc.) or using any of the featurization methods described herein. A contemporaneous probe position, an ideal probe position, and/or a deviation between, or one or more movements (such as any of the movements described further herein) are computed based on the detected imaging landmarks 806, and guidance instructions are provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 807; and subsequent images that are improved (for example, in terms of diagnostic quality and/or feature visualization) are acquired after the user has repositioned the imaging probe 808.

Figure 9:
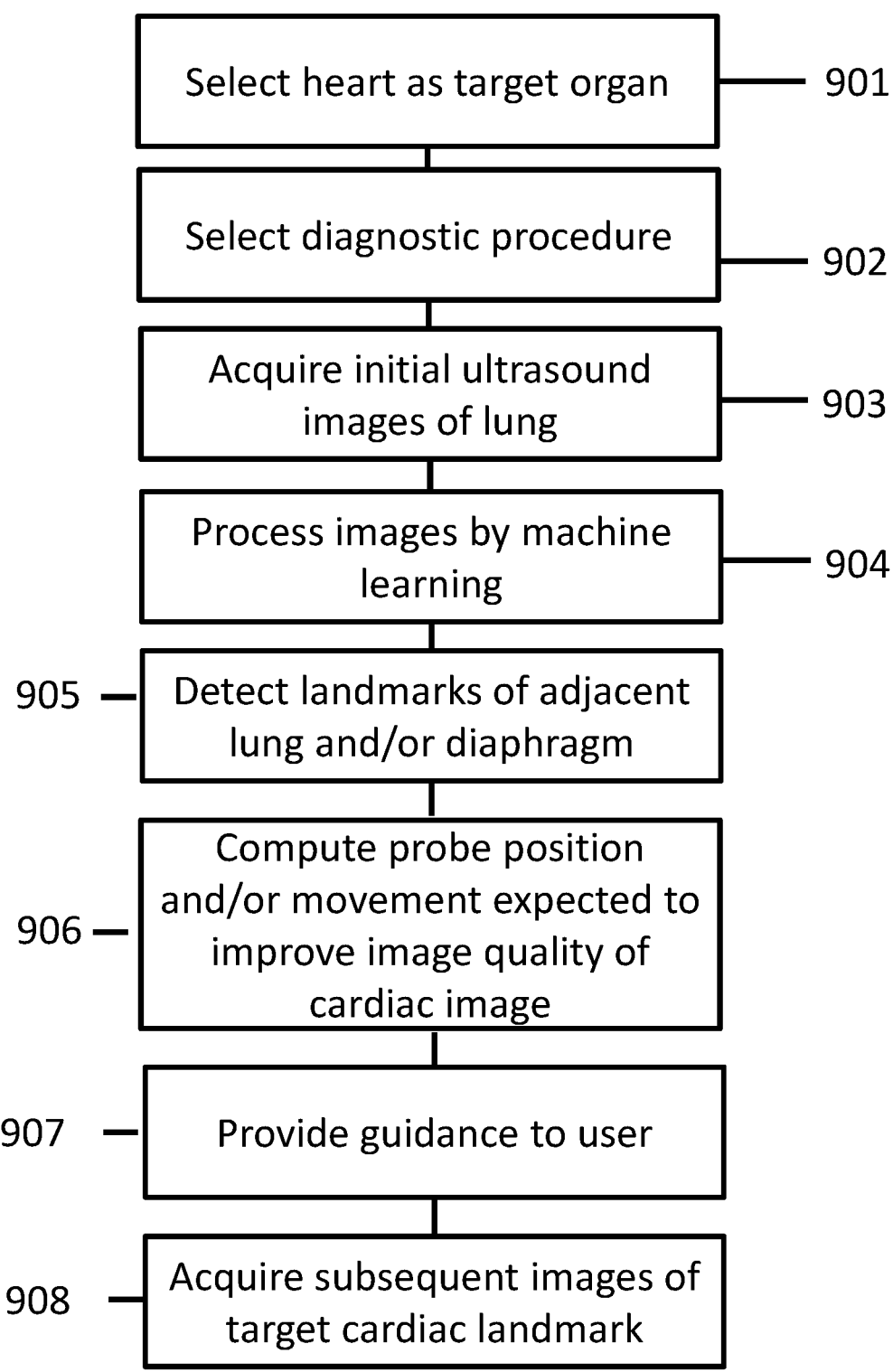
FIG. 9 illustrates a further example workflow for guiding an ultrasound imaging procedure based according to aspects described herein.

Another alternate example workflow, illustrated in FIG. 9 comprises: selecting a heart of a subject as a target organ 901; selecting a diagnostic procedure, for example, a cardiac imaging procedure for evaluation of valve function, ejection fraction, and/or classification of a pathology 902, acquiring ultrasound images a subject 903, for example, using an imaging probe of an ultrasound imaging system (e.g. using a transducer of a two-dimensional ultrasound imaging system such as a linear probe, a curvilinear probe, or a phased array probe), processing images, for example by using any of the methods described herein to detect or identify image features 904, imaging landmarks such as anatomical features or imaging artifacts of an organ: for example, visualized valves, canonical views of a heart, A-lines, B-lines, pleural-lines, rib-shadows, and/or other anatomical structures (e.g. a spine, a diaphragm, a liver, a kidney, a diaphragm or a heart, etc.) of a target organ and/or one or more adjacent organs (such as lung or bone features) 905, for example, using a machine learning model as described herein which is trained using training images comprising at least a subset of images annotated for such features by a doctor, distinguishing features from one another (e.g. distinguishing A-lines from B-lines, B-lines from the pleural line, the pleural line from rib shadows, A-lines from cardiac valves, cardiac valves from one another etc.) or using any of the featurization methods described herein. A contemporaneous probe position, an ideal probe position, and/or a deviation between, or one or more movements (such as any of the movements described further herein) are computed based on the detected imaging landmarks 906, and guidance instructions are provided to a user based on the detected imaging landmarks to guide a user to acquire an improved image of a target organ (for example, through a visual depiction of a new landing spot, or an instruction to slide, rotate, tilt, or otherwise adjust an imaging transducer according to any of the guidance movements described herein) 907; and subsequent images of a target cardiac landmark that are improved (for example, in terms of diagnostic quality and/or feature visualization) are acquired after the user has repositioned the imaging probe 908.

Diagnostic Image Quality

A particular challenge in ultrasound medical imaging is accurately determining what probe pose or movement will result in a clinical or diagnostic quality image. As used herein, an image quality (e.g. diagnostic quality or clinical quality) may be used to refer to one or more aspects of the quality of an image. In some aspects, image quality is in reference to an image that can be viewed by a trained expert or a machine learning tool in a way that anatomy is identified and a diagnostic interpretation can be made. In some aspects, image quality is in reference to an image in which the targets are displayed in a clear and well-defined manner, for example, where extraneous noise or clutter is minimal, the grayscale display shows subtle variations of tissue type and texture, frame rates are high, providing accurate depiction of tissue, aeration or lack thereof, or blood flow movement, borders between tissue types or blood flow and vessel or other structures are well resolved, ultrasound artifacts such as grating and side lobes are minimized, acoustic noise is absent, places to make measurements in the image are obvious and distinct, or any combination thereof depending on the nature of the ultrasound exam. In some aspects, image quality is in reference to an image that contains the necessary anatomical targets to represent a standard diagnostic view. In some aspects, image quality is in reference to an image in which a diseased condition, abnormality, or pathology is well visualized. For example, medical images may be labeled by healthcare professionals according to whether they are considered to have a well visualized diseased condition, abnormality, or pathology, and then used to train a machine learning algorithm to differentiate between images based on image quality. In some aspects, image quality means that some combination of these aforementioned characteristics is present.

A particular challenge in ultrasound medical imaging is accurately determining what probe pose or movement will result in a clinical or diagnostic quality image. As used herein, an image quality (e.g. diagnostic quality or clinical quality) may be used to refer to one or more aspects of the quality of an image. In some aspects, image quality is in reference to an image that can be viewed by a trained expert or a machine learning tool in a way that anatomy is identified and a diagnostic interpretation can be made. In some aspects, image quality is in reference to an image in which the targets are displayed in a clear and well-defined manner, for example, where extraneous noise or clutter is minimal, the grayscale display shows subtle variations of tissue type and texture, blood flow signals are clear and distinct, frame rates are high, providing accurate depiction of tissue or blood flow movement, borders between tissue types or blood flow and vessel or other structures are well resolved, ultrasound artifacts such as grating and side lobes are minimized, acoustic noise is absent, places to make measurements in the image are obvious and distinct, or any combination thereof depending on the nature of the ultrasound exam.

In some aspects, image quality is in reference to an image that contains the necessary anatomical targets to represent a standard diagnostic view. For example, an Apical Four Chamber view of the heart should show the apex of the heart, the left and right ventricles, the myocardium, the mitral and tricuspid valves, the left and right atria, and the interatrial septum. As another example, a long axis view of the carotid artery at the bifurcation should show the common, external, and carotid artery and the carotid bulb. In some aspects, image quality is in reference to an image in which a diseased condition, abnormality, or pathology is well visualized. For example, medical images may be labeled by cardiologists, radiologists or other healthcare professionals according to whether they are considered to have a well visualized diseased condition, abnormality, or pathology, and then used to train a machine learning algorithm to differentiate between images based on image quality.

In some aspects, image quality means that some combination of these aforementioned characteristics is present. Effective navigational guidance will need to be provided to ensure the captured ultrasound image satisfies the combination of these image quality characteristics necessary to yield an overall clinical or diagnostic quality image because, in ultrasound imaging, patient presentations can present challenges to obtaining high-resolution, low-noise images. It can be particularly challenging, for example, when trying to evaluate blood flow in the kidney of an obese agent, to get a strong enough blood flow Doppler signal because the kidney is so deep underneath fatty tissue. In a patient who has been a long-term smoker, lung disease can make it very difficult to obtain high quality cardiac images. These conditions are extremely common, and in such situations, image quality can mean an image that may be sub-optimal as far as noise and resolution, but still provides enough information for a diagnosis to be made. In a similar way, patient presentations and pathologies can make it impossible to obtain views that show all the anatomical components of a standard, canonical image. For example, a technically difficult cardiac patient may make it impossible to get an Apical Four Chamber view with all four chambers well defined, but if some images show, say, the left ventricle well, this can be considered a quality image because many critical diagnostic conclusions can be drawn from only that.

In some aspects, the anatomical views used in the present disclosure include one or more of a probe position or window, an imaging plane, and a region or structure being visualized. Examples of probe position or window include parasternal, apical, subcostal, and suprasternal notch. Examples of imaging plane include long-axis (LAX), short-axis (SAX), and four-chamber (4C). Examples of the region or structure being visualized include two-chamber, aortic valve, mitral valve, etc. For example, the anatomical views can include parasternal long-axis (LV inflow/outflow), RV inflow+/−RV outflow, parasternal short-axis (aortic valve level, mitral valve level, papillary muscle level, apical LV level), apical four-chamber, apical five-chamber, apical two-chamber, apical three-chamber, subcostal four-chamber view, subcostal short-axis and long-axis, suprasternal long-axis (aortic arch) and suprasternal short-axis (aortic arch).

Accordingly, disclosed herein are platforms, systems, and methods comprising one or more algorithms for evaluating ultrasound images to provide real-time guidance. In some aspects, the one or more algorithms comprise a probe positioning algorithm configured to estimate probe positioning relative to an ideal anatomical perspective ("probe positioning features") as well as the physical distance between the estimated and ideal probe positioning from the ultrasound imagery. The output generated by the probe positioning algorithm may be analyzed or utilized by one or more downstream algorithms. In some aspects, the one or more algorithms comprise a scoring algorithm configured to generate a computational output such as a metric or score based on the probe positioning distance. The scoring algorithm may convert the probe positioning distance into a normalized score, for example, that is proportional to the proximity between the estimated probe positioning and the ideal probe positioning, which can be used to provide real-time feedback on the quality or correctness of probe positioning. For example, the normalized score may be utilized for features such as retrospectively saving the best imagery over time and automatically capturing imagery once the score becomes sufficiently high for diagnostic purposes. In some aspects, the one or more algorithms comprise a guidance algorithm configured to estimate probe manipulations or movements that would improve the geometry of the probe positioning for a given desired canonical view of the anatomy.

The guidance algorithm may utilize the probe positioning estimated by the probe positioning algorithm and/or the positioning score calculated by the scoring algorithm. The output of the guidance algorithm can be used to determine the specific instructions to provide to the user for how to manipulate the probe. These algorithms operate together to provide real-time guidance to ultrasound the user: even a non-specialist user may follow prescriptive guidance and optimize the positioning score to get a point where the diagnostic quality is achieved and the corresponding ultrasound images are captured automatically. The non-specialist user frequently encounters non-ideal probe positioning. The ultrasound guidance workflow can include a positioning algorithm to estimate the positioning relative to the ideal, based on input imagery. A scoring algorithm may be used to calculate a quality metric or score based on the positioning generated by the positioning algorithm. A guidance algorithm utilizing features of adjacent organs can then be used to produce probe navigational guidance for reducing the difference between the current positioning of the probe and the ideal positioning. Algorithms then produce real-time guidance. This guidance can be presented to the user via a user interface in real-time to provide timely guidance for the user to improve image quality. This process may be repeated to arrive at the final, ideal positioning that produces diagnostic quality echocardiogram. In some cases, images that successfully achieve diagnostic quality are captured automatically during this process.

Ultrasound Guidance

Disclosed herein are platforms, systems, and methods that provide navigational guidance to users to instruct them how to hold and manipulate the probe in order to get diagnostic or clinical quality images sufficient to make medical and/or diagnostic decisions. The conditions and the nature of ultrasound imaging create various problems for navigation assistance ultrasound technologies. Methods for providing guidance to users for ultrasound acquisition are faced with the image quality challenges listed above in order to provide high quality images sufficient to draw medical diagnoses or conclusions. One technical challenge is the guidance must function in real-time at sufficiently high frame rates to enable effective navigational guidance to the user (e.g. as high as 60 frame per second or higher). Another challenge is the guidance needs to function effectively while the user is moving the probe in a variety of manners and directions such that the image is rapidly changing. Another challenge that frequently arises is providing effective navigational guidance despite the ambiguity of suboptimal images acquired during the ultrasound imaging procedure, where a human expert or a machine learning tool may not always be able to recognize the structures. There may often be multiple movements that a user should make in order to get a quality image of a particular target. For example, the user may be trying to image the aortic valve from the parasternal window. The movements they need to make to get a good image might include rotating the probe counterclockwise, sliding the probe up on the patient, and rocking the probe towards the index marker on the probe. Providing instructions on all of these possible movements, in a coherent and usable manner, when the user is at the same time moving the probe in correct or incorrect ways is difficult. This difficulty is amplified by the fact that the movement guidance instructions estimated by a guidance algorithm inevitably contain some uncertainly and error. There may even at times be multiple legitimate guidance calculations that are estimated simultaneously even though they contradict one another. For example, a particular structure or view may be achieved by rotating the probe clockwise, or it may be achieved by rotating the probe counter-clockwise. Whether one path is better than another can change rapidly based on such things as, patient breathing, patient movement, heart motion, blood vessel pulsations, or the user moving the probe. Collectively, these challenges significantly reduce the effectiveness of ultrasound navigation methods.

Accordingly, the platforms, systems, and methods disclosed herein provide navigational guidance to users for probe movement and/or manipulation for obtaining diagnostic or clinical quality images. In particular, in certain aspects, the navigational guidance is improved through an omnidirectional guidance feature that compensates and/or mitigates potentially contradictory and/or fluctuations in navigational guidance that can arise due to any of the above-mentioned technical challenges. One advantage provided by the present disclosure is the provisioning of navigational guidance when there are multiple movements at one time that can be made. Another advantage is providing navigational guidance when the image is rapidly changing because of constant and unpredictable patient movement, tissue movement, probe movement by the user, or any combination thereof. Another advantage is providing navigational guidance when there is substantial uncertainty or the navigation tool cannot fully overcome uncertainty or erroneous movement instructions. Another advantage is providing real-time probe movement instructions to users in a manner that addresses these problems but produces user feedback that is smooth, logical, and not distracting or confusing.

In some cases, when multiple instructions may be needed, the most important movement instruction (e.g., having the highest likelihood or probability of improving image quality) is selected and provided to the user. The selection of which one or perhaps one or two, of several viable movements should be displayed to the user can be determined by looking at a time sequence of ultrasound frames, and determining which guidance movement instruction occurs most frequently. For example, the device could collect two seconds worth of image frames at a frame rate of 60 fps for a total of 120 frames. If the "Rotate Clockwise" instruction is determined to be the appropriate movement guidance instruction 100 times and the "Slide Medially" instruction is calculated 20 times, the "Rotate Clockwise" instruction would be displayed as the instruction that was calculated most frequently within the time frame. This time frame can be a certain time duration during which a plurality of movement instructions are evaluated to determine the specific instruction to be displayed. Alternatively, the plurality of movement instructions may be evaluated based on a certain number of the most recent frames. For example, the most important instruction may be selected based on evaluation of the most recent plurality of movement instructions such as the most recently captured 120 image frames. The duration and/or the number of frames used for this selection of the most important instruction can be set at a number that provides satisfactory smoothing of the guidance instructions. Then, once the most important probe movement has been made, the next most important movement instruction may be provided to the user (e.g., via a user interface such as a digital display integrated into a handheld ultrasound device or on a separate display communicatively coupled to the ultrasound device), and the process is repeated until a quality image is obtained.

In some cases, when the image is rapidly changing because of constant and unpredictable patient movement, tissue movement, or probe movement by the user, a specific movement instruction is provided through the user interface for a minimum duration. Without this, different instructions could flash up on the screen many times a second, or be provided audibly or through haptic feedback, thereby producing confusing, distracting, and unusable feedback to the user. In some cases, the specific movement instruction may be configured to occur over a set period of time or a minimum period of time (e.g., a minimum threshold). In some cases, the movement instruction occurs over some number of sampling instances.

In some cases, to address the problem that the navigation tool cannot fully overcome uncertainty or erroneous movement predictions, a threshold measurement is used to only display movements instructions to the user that pass the threshold. For example, a certain threshold number or threshold duration of a particular movement instruction for improving diagnostic or clinical image quality may be required (out of a total number or total duration of sampling instances) before the instruction is displayed to the user in order to avoid confusing the user. Therefore, to provide user feedback that is smooth, logical, and not distracting or confusing, one approach is to use a threshold to select a single movement most likely to overcome an image quality deficiency, require that such a movement meet a threshold amount or value to be passed to the user, not provide other movement possibilities to the user simultaneously, and apply a time filter (e.g., a minimum time duration) or number filter (e.g., a minimum number of images) to ensure a defined movement has been identified and is persisting. In some cases, the single view threshold-based process includes the steps of image acquisition, probe position guidance detection or determination, detecting at least one corrective movement to obtain the clinical quality image from the current probe position, determining if the detected probe position guidance movement instruction meets a certain threshold or requirement, comparing multiple probe position guidance movement instructions to determine which instruction is detected over a threshold level more than other instructions (e.g., a particular movement instruction is determined to be the corrective movement for obtaining the clinical quality image most frequently during a certain time window or duration), and present the one probe position guidance movement instruction.

In some cases, the image the user is trying to obtain is a parasternal long axis view of the heart. The navigation software has determined that the user is relatively close to an acceptable image. The user is informed of this by the quality meter in the upper left corner of the screen. The two triangular tick marks on the meter represent a reliably diagnostic image. The multiple horizontal bars approach the tick marks and change colors (e.g., turn green) to indicate that the image is good and close to reliably diagnostic. The probe movement instruction that has been determined to best most appropriate to improve the image is that the user should rotate the probe counter clockwise slowly. This is displayed as a text message and in the form of an icon. Note that just one instruction is provided to the user at a time. In this implementation, the instruction is designed to change only after a probability threshold and timing filter are met.

This method may arrive at this single instruction by using an image processing or machine learning model that compares the current image to a desired image. It may use an anatomical model of the spatial relationship of the deficient current image to the desired optimal image to determine probe movement instructions. It may use a model that correlates the current deficient image probe position to the probe position of the desired optimal image to determine probe movement instructions. These estimates will produce multiple possible instructions. These include different movement types that are compatible with getting a good image, but can also include contradictory movements that the model can't disambiguate. A threshold is applied to select one instruction that achieves the highest confidence level of the various possibilities returned by an algorithm. This class of instruction then is held for presenting to the user pending a continual monitoring of the image to confirm over some number of instances, such as a frame, number of frames, time period, or number of sampling instances, that the instruction is accurate. Feedback can be visual, such as a text display, graphical icon, or audible, or haptic.

The current navigation solutions are insufficient to address the particular technical problems recognized in the instant disclosure because they only provide one instruction at a time or only a limited number of instructions, which can result in certain technical challenges in providing suitable instructions to the user. The limitation on instructions shown to the user may utilize a threshold to decide which of one or a limited number of instructions to display to the user. There may be a delay in displaying instructions to users because a time filter is used to avoid rapidly flashing different instructions to users. If multiple instructions are provided without using thresholding, or instructions without using time filters, then the feedback would be unusable or difficult to interpret. For example, there would be rapidly appearing and disappearing or changing text messages or graphic icon changes (or other guidance instructions/indications) as the probe is moved and captures numerous images, some of which are of low quality and therefore produce low quality calculated navigational guidance instructions.

By contrast, the platforms, systems, and methods disclosed herein provide for improved navigational guidance that overcomes the limitations of previous approaches. In one aspect, the guidance utilizes a threshold that looks for a probe movement instruction to occur over a period of time or a number of computations to select among multiple alternatives that may or may not be used, or may be adjustable. The guidance for probe navigation or movement instructions can be instantaneously provided to the user in real-time as they are operating the ultrasound probe. In some cases, the guidance for multiple probe movements are provided simultaneously. The guidance may include feedback or additional information on probe movement instructions that have differing probabilities of being accurate, even ones that contradict each other. The guidance may be presented via a graphical method that minimizes distracting visual information. The graphical display may incorporates a plurality of movement instructions in an intuitive manner. In some cases, the display uses one of several methods to inform the user of the confidence level or importance of the various movements. For example, the confidence level or importance of one or more movements (e.g. corresponding to improvement in image quality expected to be obtained through the movement) can be graphically represented with increasing or decreasing screen brightness (e.g. increased brightness for higher confidence movements), colors (e.g. red for low, yellow for intermediate, and green for high likelihood of being accurate), or it could be with different types of graphical filling or markers (e.g. the graphical density of filling in an icon). Different parts of the guidance graphic could pulse or flash to indicate movement. Colors and icons could be of varying transparency and these parameters may change as the user moves to the correct position, for example, the colors and icons could solidify as the probe approaches the correct position. In some cases, the navigational guidance comprises instructions or contextual information not strictly related to probe movements, such as patient breathing or body position instructions, or ultrasound system setting instructions such as depth or gain. In some cases, the instructions do not have thresholds correlated with image quality.

In some cases, the ultrasound navigation device is configured to provide many types of probe movement instructions, and other scanning instructions. Examples of instructions include such pose changes as: rotate the probe clockwise or counterclockwise, slide (translate) the probe up towards the patient's head, down towards the patient's feet, laterally towards the patients side, medially towards the patient's midline. Instructions can include telling the user to tilt the ultrasound beam up towards the head, down towards the feet, laterally or medially. This instruction can also be provided in relationship to the back or "tail" of the physical probe. For example if the instruction calls for the beam to be aimed up towards the head, the instruction could be to move the probe tail down. In some cases, the probe comprises an index marker (e.g., on one side). This can correspond to a graphical display on one side of the image on the screen. Accordingly, the user can be instructed to rock the probe towards this marker or away from this marker. The user can also be instructed to apply more or less pressure to the probe as it is pressed against the patient.

Other instructions not strictly related to probe position may be provided, including ultrasound acquisition parameters such as changing the scanning depth of field setting or increasing or decreasing image gain. In some cases, patient instructions are provided, for example, instructions for the patient change their breathing pattern or to move or adjust the patient's body or body positioning.

In some cases. After image acquisition by the ultrasound probe, the probe position guidance is determined or detected. Compared to a clinical quality probe position for a single target view, it is determined whether the probe position guidance detector detects or determines at least one corrective movement to obtain the clinical quality image from the current probe position. Next, the one or more probe position guidance movement instructions that are determined in the previous step are presented to the user to provide navigational guidance of the probe for the single target view.

After image acquisition by the ultrasound probe, the probe position guidance is determined or detected. Compared to a clinical quality probe position for multiple target views, it is determined whether the probe position guidance detector detects or determines at least one corrective movement to obtain the clinical quality image from the current probe position for at least one but potentially multiple target views. Next, the one or more probe position guidance movement instructions that are determined in the previous step are presented to the user to provide navigational guidance of the probe for at least one or a plurality of the multiple target views.

In some cases, the graphical display contains the four main movements, tilt beam (towards head, towards feet, lateral or medial), slide (up, down, lateral medial), rotate (clockwise, counter clockwise), and rock (towards a probe index marker, away from a probe index marker). While is shown with all the movement indicators in the same color, they could have different colors, different brightness levels, different filling types, or any combination thereof to show importance. Dynamic graphical features may be included, for example, the movement indicators may pulsate or fade in relation to the estimated importance or likelihood computed for the corresponding navigational guidance movement. One or more of the instruction components could be changing rapidly, continuously, and without delays, and this unique combination of multiple navigational movement instructions being presented simultaneously together with indicators of their respective importance provides a coherent interface that enables a user to efficiently understand the navigational options that are available and therefore make fast and accurate decisions in adjusting probe movement.

In some cases, a black and white version of the graphical display is shown. In this illustrative example, the graphical display contains shaded icons depicting the four main movements, tilt beam (towards head, towards feet, lateral or medial), slide (up, down, lateral medial), rotate (clockwise, counter clockwise), and rock (towards probe index marker, away from probe index marker), where the darkness of the icon fill reflects a higher ranking in terms of priority of making the movement. Accordingly, rotate clockwise would be the most important move, followed by slide down, followed by tilt the beam to the right. While the illustration is in black and white, such information can also be conveyed by any alternative methods disclosed herein such as through modulating the visual movement indicators to be shown in various colors according to a priority ranking.

Additional information may be added, including non-movement instructions. For example, an icon may represent patient breathing state or pressure on the probe against the patient. This additional information could be updated continuously and displayed in real-time as the image analysis module and/or machine learning device detects potential changes the user could make.

Another implementation of this guidance system would be to utilize the movement instruction method and display to provide guidance to multiple anatomical views at once. The dial-like graphical display could be replicated multiple times on the display, one each for a particular view. The algorithm can display the movement instructions for the multiple views simultaneously. This would be impractical using current methods. For example, a user might be scanning a parasternal short axis view of the heart at the mitral valve level. Tilting the beam up could produce an image of the aortic valve, tilting the beam down could produce an image of the left ventricle at the papillary muscle level. Each option could be displayed without causing confusion to the user. This embodiment could be implemented by replicating the movement instruction graphic for each view, or alternatively, it could be implemented by placing a text or icon marker for a view at a position on a single movement instruction graphic. In some cases, one or more of the anatomical views are user selected via the user interface before or during the ultrasound examination. This allows a user to determine the anatomical views for which probe movement or guidance instructions will be provided.

In some cases, multiple movements to multiple views are provided simultaneously. Both the movement graphic filled in black and the associated target anatomical view next to the movement graphic are shown for three different views. From the current position, slide up will produce a parasternal short axis at the aortic valve level, rotate counterclockwise will produce a parasternal long axis view (papillary muscle level), and slide down will produce the parasternal short axis. Alternatively, this graphical display could be implemented as a separate movement set of icons or visual indicators produced for each view instead of the multiple views sharing the same set of movement icons or visual indicators. In some cases, movements are directed to move from one organ to an adjacent organ.

In some cases, a graphical display shows the following anatomical target views: PLAX (parasternal long axis), PSAX AV (parasternal short axis aortic valve level), PSAX MV (parasternal short axis mitral valve level), PSAX PM (parasternal short axis papillary muscle level), AP5 (apical five chamber), SC4 (subcostal four chamber), SC IVC (subcostal inferior vena cava), AP4 (apical four chamber), AP3 (apical three chamber), and AP2 (apical two chamber). In some cases multiple anatomical views, any given view can include one or more of the following data parameters: echo distance (ED) corresponding to the distance from the current probe position to the optimal position, image quality (IQ) corresponding to the clinical image quality of the image derived from echo distance, prescriptive guidance types (PG types) corresponding to the different types of probe movements identified and qualified, and confidence that a particular probe movement type is correct (confidence).

Nonlimiting examples of suitable methods for determining confidence comprise identification of one or more specific image frames which have a lower error rate for generating one probe movement type than another. The probe movement associated with the lower error rate for the specific image can then be given a higher confidence level compared to one or more probe movements associated with a higher error rate.

Confidence can be based on an echo distance basis of one or more particular probe movements. The echo distance basis can comprise identification of a confidence expectation based on a particular echo distance parameter, such as the magnitude of a movement needed to reach a particular pose with a view quality meeting a quality threshold, a movement vector that is shorter or easier for a user to make than another echo distance/probe movement combination, or a metric proven during algorithm training to more often result in acceptable image quality.

An echo distance parameter can have a threshold point that determines whether an image has a diagnostic quality or a non-diagnostic quality. The threshold point can be set based on a selected, particular, anatomical target, pathology, clinical question or view. The confidence value for a particular probe movement with a shorter echo distance or expected to be over a given diagnostic threshold can be higher than for one or more probe movements with longer echo distances or expected to result in an images below the threshold quality. The threshold values can be adjusted for different anatomical targets, ultrasound scanning modes, views, clinical questions, image quality goals, or other parameters, and probe movements that exceed these thresholds more than others can be given a higher confidence level.

Confidence can be determined by mapping, or transformation of the echo distance to an image quality score. This transformation can be implemented so that the IQ scores are optimized or customized for a particular view, pathology, patient condition, clinical question, or therapeutic plan. The transformation can be adapted to accomplish one or more of these optimization goals. IQ scores can be adapted through transformation parameters to give one or more probe movements a higher confidence value than alternative probe movements.

For example, a user could be scanning a view that includes a target anatomical feature such as an aortic valve, or following a protocol that includes assessing the target anatomical feature. An acquired image can produce an echo distance that comprises one or more IQ scores for the target anatomical feature (e.g. the aortic valve), and can further comprise one or more additional IQ scores for alternate target anatomical features (e.g. for the mitral valve if the primary target anatomical feature was the aortic valve). Anatomical features can be classified as primary targets and secondary targets or may be ranked according to priority by assigning each target or groups of targets one of a plurality of unique target priority identifiers. Ranked targets can be assigned different threshold values based upon their assigned rank. For example, when the primary target is the aortic valve, the echo distance to IQ score mapping could have a different threshold to trigger a probe movement for the aortic valve instead of a secondary or lower ranked target such as the mitral valve, and the movement towards the primary target could be given a higher confidence value.

Some approaches use thresholding combined with a form of time averaging and smoothing to give the user feedback that they can absorb without distraction of confusing information. However, disclosed herein are platforms, systems, and methods that address the need for a smooth user experience while providing instantaneous and multiparameter instruction by using signal processing techniques such an exponential moving average and/or a Kalman filter. This can maintain the instantaneous feedback to the user with a very gradual blending of the guidance features without requiring cutoff thresholds to be used.

This innovative approach can utilize novel uses of audio to provide guidance. The graphic display method described herein addresses the problem of getting instantaneous guidance feedback for multiple movements in a way that does not confuse the user with too much stimuli. As disclosed herein, in certain aspects, audio methods augment or substitute for the visual method. The use of audio guidance may be advantageous because the brain may process diverse audio stimuli that are provided without temporal integration better than it can process such inputs visually.

Audio feedback can be provided to the user in various forms. Examples include simple verbal messages, such as producing an instruction to "Rotate Clockwise" through a speaker. Other examples include providing an audible beep to a user to indicate that a successful image has been captured. Non-verbal audible feedback may be used, for example, a speaker for producing various tones or sounds associated with a probe guidance instruction or image improvement step. The feedback signal could have an audible tone that increases or decreases frequency as the probe is moved from one position to another, varying with whether the direction is correct or incorrect for getting a good image. Such approaches may also rely on weighting of potential movement instructions, some form of temporal averaging or smoothing, and of selection of one or very few of a number of potential legitimate probe movements. These techniques may be used to avoid distracting and confusing the user with an overwhelming amount of verbal or tonal signals.

In some aspects, the platforms, systems, and methods disclosed herein provide for the user of an audio headset, which allows much more sophisticated audio signals to be used and implemented. In some cases, the use of an audio headset enables the left and right channels to be used to provide movement instructions relative to the left and right of the patient. For example, "Slide medial" instructions for scanning the heart, which anatomically means slide leftwards towards the middle of the probe from the left side of the body where the heart is being scanned, may be played as audio in the left channel only so only the left ear hears the instruction.

In some cases, verbal instructions and/or non-verbal instructions or sounds are used. If the instructions are continuous and of multiple types, verbal sound will be difficult for the user to comprehend. Alternatives to verbal sounds could be skeuomorphic, which uses sounds that are associated with real-world objects. For example, the playing of a slide whistle sound in the right ear could corresponding to instructions to slide right. The playing of a slide whistle sound in both ears increasing in frequency could correspond to instructions to slide up. In this approach, multiple instructions with different sound types could coexist and be provided simultaneously. Exponential moving average and/or Kalman filters, as mentioned above in relation to the visual feedback, could be used to smooth the output. "Sonic metaphors" where artificial tones or sounds that are not directly associated with existing real-world sounds, but which have an intuitive ability to convey a direction, could be used instead of skeuomorphic sounds.

In some cases, the audio headset uses 3D sound techniques. 3D audio or immersive sound is used in movies, video games, navigation for the blind, and other applications. The 3D audio mimics the way a person hears by providing three-dimensional localization of sound. 3D audio played through headsets can present the hearer with a sense that a sound is directional as well as conveying a sense of distance. As disclosed herein, 3D audio can be used to convey directional movement. 3D audio instructions can, for example, play a sliding sound the user perceives as up or down, which exceeds what simple left-right speakers can do. For example, 3D audio instructions can make a sound appear to be moving in a circular manner, such as a clockwise direction, starting on the right, then above, then left, then below.

The audio techniques for providing instruction or navigational guidance disclosed herein can be combined with haptic feedback. In some cases, the haptic feedback is delivered through the headset. Current haptic feedback methods focus on providing the feedback through the handheld probe, with the idea that various vibrations could tell the user how to move the probe. However, the platforms, systems, and methods disclosed herein can utilize haptic feedback alone or in combination with the visual feedback and/or audio feedback.

Accordingly, disclosed herein are platforms, systems, and methods that provide fast and reliable ultrasound guidance instructions without relying on thresholding, single instruction feedback, and timing filters.

Machine Learning Algorithms

Disclosed herein are platforms, systems, and methods that provide ultrasound image classification using machine learning algorithm(s). In particular, in some aspects, the machine learning algorithms include deep learning neural networks configured for evaluating ultrasound images. The algorithms can include one or more of a positioning algorithm, a scoring algorithm, a probe guidance algorithm, and an intrinsic image quality algorithm. The positioning algorithm can include one or more neural networks that estimate probe positioning relative to an ideal anatomical view or perspective and/or a distance or deviation of a current probe position from an ideal probe position. The intrinsic image quality algorithm may determine that intrinsic image quality is below a threshold based in part on a determination by a positioning algorithm that one or more images have been acquired at a probe position expected to obtain a clinical quality image.

The development of each machine learning algorithm spans three phases: (1) dataset creation and curation, (2) algorithm training, and (3) adapting design elements necessary for product performance and useability. The dataset used for training the algorithm can be generated by obtaining ultrasound images that are then curated and labeled by expert radiologists and/or pulmonologists, for example, according to lung segment, score, presence of various image features such as A-lines, B-lines, a pleural line, rib shadows, presence of tissues from other organs (e.g. heart, liver, kidneys, etc.), and other metrics. Each algorithm then undergoes training using the training dataset, which can include one or more different target organs and/or one or more different views of a given target organ. The training dataset for the positioning algorithm may be labeled according to a known probe pose deviation from the optimal probe pose.

A machine learning model can comprise a supervised, semi-supervised, unsupervised, or self-supervised machine learning model. In some cases, the one or more ML approaches perform classification or clustering of the MS data. In some examples, the machine learning approach comprises a classical machine learning method, such as, but not limited to, support vector machine (SVM) (e.g., one-class SVM, linear or radial kernels, etc.), K-nearest neighbor (KNN), isolation forest, random forest, logistic regression, AdaBoost classifier, extra trees classifier, extreme gradient boosting, gaussian process classifier, gradient boosting classifier, light gradient boosting, linear discriminant analysis, naïve Bayes, quadratic discriminant analysis, ridge classifier, or any combination thereof. In some examples, the machine learning approach comprises a deep leaning method (e.g., deep neural network (DNN)), such as, but not limited to a fully-connected network, convolutional neural network (CNN) (e.g., one-class CNN), recurrent neural network (RNN), transformer, graph neural network (GNN), convolutional graph neural network (CGNN), multi-level perceptron (MLP), or any combination thereof.

In some aspects, a classical ML method comprises one or more algorithms that learns from existing observations (i.e., known features) to predict outputs. In some aspects, the one or more algorithms perform clustering of data. In some examples, the classical ML algorithms for clustering comprise K-means clustering, mean-shift clustering, density-based spatial clustering of applications with noise (DB-SCAN), expectation-maximization (EM) clustering (e.g., using Gaussian mixture models (GMM)), agglomerative hierarchical clustering, or any combination thereof. In some aspects, the one or more algorithms perform classification of data. In some examples, the classical ML algorithms for classification comprise logistic regression, naïve Bayes, KNN, random forest, isolation forest, decision trees, gradient boosting, support vector machine (SVM), or any combination thereof. In some examples, the SVM comprises a one-class SMV or a multi-class SVM.

In some aspects, the deep learning method comprises one or more algorithms that learns by extracting new features to predict outputs. In some aspects, the deep learning method comprises one or more layers. In some aspects, the deep learning method comprises a neural network (e.g., DNN comprising more than one layer). Neural networks generally comprise connected nodes in a network, which can perform functions, such as transforming or translating input data. In some aspects, the output from a given node is passed on as input to another node. The nodes in the network generally comprise input units in an input layer, hidden units in one or more hidden layers, output units in an output layer, or a combination thereof. In some aspects, an input node is connected to one or more hidden units. In some aspects, one or more hidden units is connected to an output unit. The nodes can generally take in input through the input units and generate an output from the output units using an activation function. In some aspects, the input or output comprises a tensor, a matrix, a vector, an array, or a scalar. In some aspects, the activation function is a Rectified Linear Unit (ReLU) activation function, a sigmoid activation function, a hyperbolic tangent activation function, or a Softmax activation function.

The connections between nodes further comprise weights for adjusting input data to a given node (i.e., to activate input data or deactivate input data). In some aspects, the weights are learned by the neural network. In some aspects, the neural network is trained to learn weights using gradient-based optimizations. In some aspects, the gradient-based optimization comprises one or more loss functions. In some aspects, the gradient-based optimization is gradient descent, conjugate gradient descent, stochastic gradient descent, or any variation thereof (e.g., adaptive moment estimation (Adam)). In some further aspects, the gradient in the gradient-based optimization is computed using backpropagation. In some aspects, the nodes are organized into graphs to generate a network (e.g., graph neural networks). In some aspects, the nodes are organized into one or more layers to generate a network (e.g., feed forward neural networks, convolutional neural networks (CNNs), recurrent neural networks (RNNs), etc.). In some aspects, the CNN comprises a one-class CNN or a multi-class CNN.

In some aspects, the neural network comprises one or more recurrent layers. In some aspects, the one or more recurrent layers are one or more long short-term memory (LSTM) layers or gated recurrent units (GRUs). In some aspects, the one or more recurrent layers perform sequential data classification and clustering in which the data ordering is considered (e.g., time series data). In such aspects, future predictions are made by the one or more recurrent layers according to the sequence of past events. In some aspects, the recurrent layer retains or "remembers" important information, while selectively "forgets" what is not essential to the classification.

In some aspects, the neural network comprise one or more convolutional layers. In some aspects, the input and the output are a tensor representing variables or attributes in a data set (e.g., features), which may be referred to as a feature map (or activation map). In such aspects, the one or more convolutional layers are referred to as a feature extraction phase. In some aspects, the convolutions are one dimensional (1D) convolutions, two dimensional (2D) convolutions, three dimensional (3D) convolutions, or any combination thereof. In further aspects, the convolutions are 1D transpose convolutions, 2D transpose convolutions, 3D transpose convolutions, or any combination thereof.

The layers in a neural network can further comprise one or more pooling layers before or after a convolutional layer. In some aspects, the one or more pooling layers reduces the dimensionality of a feature map using filters that summarize regions of a matrix. In some aspects, this down samples the number of outputs, and thus reduces the parameters and computational resources needed for the neural network. In some aspects, the one or more pooling layers comprises max pooling, min pooling, average pooling, global pooling, norm pooling, or a combination thereof. In some aspects, max pooling reduces the dimensionality of the data by taking only the maximums values in the region of the matrix. In some aspects, this helps capture the most significant one or more features. In some aspects, the one or more pooling layers is one dimensional (1D), two dimensional (2D), three dimensional (3D), or any combination thereof.

The neural network can further comprise of one or more flattening layers, which can flatten the input to be passed on to the next layer. In some aspects, a input (e.g., feature map) is flattened by reducing the input to a one-dimensional array. In some aspects, the flattened inputs can be used to output a classification of an object. In some aspects, the classification comprises a binary classification or multi-class classification of visual data (e.g., images, videos, etc.) or non-visual data (e.g., measurements, audio, text, etc.). In some aspects, the classification comprises binary classification of an image (e.g., contrast needed or contrast not needed). In some aspects, the classification comprises multi-class classification of a text (e.g., identifying hand-written digits)). In some aspects, the classification comprises binary classification of a measurement. In some examples, the binary classification of a measurement comprises a classification of a system's performance using the physical measurements described herein (e.g., normal or abnormal, normal or anormal).

The neural networks can further comprise of one or more dropout layers. In some aspects, the dropout layers are used during training of the neural network (e.g., to perform binary or multi-class classifications). In some aspects, the one or more dropout layers randomly set some weights as 0 (e.g., about 10%, 20%, 30%, 40%, 50%, 60%, 70%, 80% of weights). In some aspects, the setting some weights as 0 also sets the corresponding elements in the feature map as 0. In some aspects, the one or more dropout layers can be used to avoid the neural network from overfitting.

The neural network can further comprise one or more dense layers, which comprises a fully connected network. In some aspects, information is passed through a fully connected network to generate a predicted classification of an object. In some aspects, the error associated with the predicted classification of the object is also calculated. In some aspects, the error is backpropagated to improve the prediction. In some aspects, the one or more dense layers comprises a Softmax activation function. In some aspects, the Softmax activation function converts a vector of numbers to a vector of probabilities. In some aspects, these probabilities are subsequently used in classifications, such as classifications of one or a plurality of image features comprised in one or a plurality of ultrasound images of a lung of a subject.

Computer Systems

Figure 10:
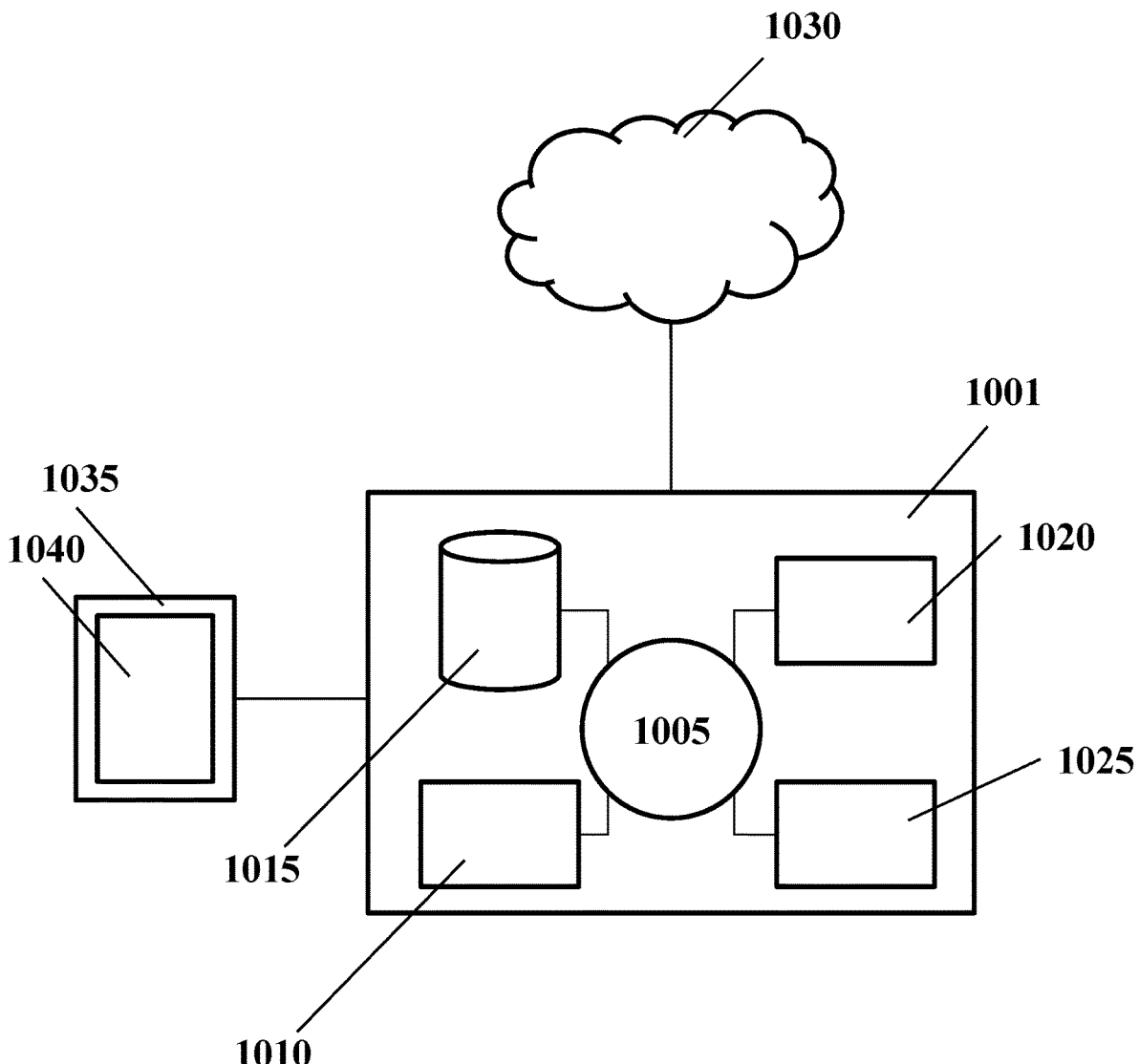
FIG. 10 shows a computer system that is programmed or otherwise configured to implement methods provided herein.

The present disclosure provides computer systems that are programmed to implement methods of the disclosure. FIG. 10 shows a computer system 1001 that is programmed or otherwise configured to assess whether an ultrasound enhancing agent is expected to improve image quality according to any of the methods described herein. The computer system 1001 can regulate various aspects of the present disclosure. The computer system 1001 can be an electronic device of a user or a computer system that is remotely located with respect to the electronic device. The electronic device can be a mobile electronic device.

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user (e.g., a professional sonographer or an untrained technician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, providing a user with an indication of whether or not an ultrasound enhancing agent is needed to improve an intrinsic image quality. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, be configured to perform any of the methods described herein.

EXAMPLES

Example 1: Machine Learning Models for Guidance of Lung and Cardiac Imaging Procedures Utilizing Adjacent Organ Imaging Landmarks A healthy lung is aerated, so it was long thought to be impractical to use ultrasound for lung imaging. However, a number of pulmonary pathologies are associated with a loss of aeration due to fluid accumulation, inflammation, infection, fibrosis, and/or atelectasis. In many of these cases, the lung parenchyma and associated artifacts can be observed using ultrasound. While lung ultrasound is not a new field, its development has accelerated substantially in recent years as a result of a combination of the affordability of point-ofcare devices as well as relevance for investigating COVID19-associated pneumonia.

Lung imaging is typically done with a curvilinear probe and sometimes with a linear probe as well. The use of a phased array probe is rare but in resource/time constrained settings where a single probe may be preferred, phased array probes may be used. The example model has mostly been trained with images from curvilinear and phased array probes, along with the butterfly probe, which can be considered a hybrid of the two.

Probes used by systems and methods described herein may comprise a linear probe, a curvilinear probe, and/or a phased array probe.

The original bedside lung ultrasound in emergency (BLUE) protocol, which consisted of 12 zones for overall lung assessment, including anterior, lateral, and posterior views, is often used [doi.org/10.1186/2110-5820-4-1]. Other studies suggested a simplified version of this protocol consisting of only 8 zones [doi.org/10.1186% 2F1476-7120-12-25], with one recent study in COVID-19 patients showing the 8-zone protocol to be comparable to the full 12-zone protocol for outcome prediction in this setting [doi.org/10.1002% 2Fjum.15849]. Given this evidence for comparability of these protocols, combined with the ease of implementation of an 8-zone protocol, especially for novice ultrasound users, the development of an example machine learning algorithm with collection and interpretation of data from the 8-zone protocol was chosen for implementation of the example embodiment of methods and systems described herein. An 8-zone lung protocol consists of four chest areas per side, commonly referred to as "zones": Zones 1/5 and 2/6 denote the upper anterior and lower anterior chest, whereas areas 3/7 and 4/8 denote the upper lateral and lower lateral chest, respectively.

For healthy patients, normally aerated lung parenchyma provides little to no echogenicity. Thus, it is typical to see images of upper anterior and lateral zones showing a combination of shallow anatomy (ribs, intercostal muscle layers, and pleural line) and sonographic artifacts (A-lines, rib shadows) within the lung space. When the probe is held perpendicular to the pleural surface, A-lines are observed. These are reverberation artifacts caused by the strong reflection of sound waves at the interface of the visceral pleura and the lung parenchyma.

Additionally, large anechoic "rib shadows" are observed in regions distal to ribs due to the blocking of sound waves by the ribs themselves. A canonical image observed when the probe is held longitudinally (across the ribs) consists of two rib shadows on either side of the center of the FOV, with the pleural line visible in the center of the FOV. This has colloquially been termed the "bat sign".

Because there are relatively few imaging landmarks available for lung imaging, features of adjacent organs such as the heart are combined with lung image features when training a machine learning model for probe navigation which is both capable of imaging multiple organs in a single procedure, and is robust even to extremely off-axis initial probe positioning.

Pleural-Lines, a-Lines, Rib-Spaces

For normal patients, in the anterior and anterolateral regions of the chest, the pleural lines, rib/rib-shadows and possibly a-lines are usually visible. The pleural line represents the interface between tissue (pleura) and the aerated lung. No structures are seen below the pleura in a normal lung; instead, artifacts are observed. Below the pleural line, similar horizontal lines known as a-lines are seen. These are reverberation artifacts of the pleural line. Even for a normal lung, A-lines do not always appear. The probe must make good contact and should be held at a good angle relative to the rib-spaces for a-lines to present nicely. To both sides of the pleura, anechoic (dark) areas that are rib-shadows can be seen. Together, the pleura and the rib shadows—with the pleura situated centrally and 2 rib shadows flanking the pleura—is called the bat sign.

B-Lines

For patients with pathologies, another artifact begins to appear in these anterior/upper zones called the b-lines. Instead of horizontal artifacts, vertical artifacts that cover the space below the pleura, all the way to the bottom of the US cone area, will now be seen.

B-lines can appear discretely as one or more distinct lines and confluently where multiple lines coalesce into one or more b-lines. Clinically, three or more b-lines are considered significant. However, accounting for the confluent b-lines if they exist is complex and there are currently no widely accepted clinical guidelines for this. The key thing to note is that quantification and tracking of b-lines' score holds a great deal of clinical value.

Consolidation

As even more fluid gathers in the lung due to various pathologies, the lung starts getting 'consolidated' and air is replaced more and more by fluid. The consolidated areas of the lung then transmit US waves but only until the boundary of the consolidated and aerated areas. Sometimes, the entire lobe can be consolidated if there's too much fluid outside the lung during a very severe pleural effusion (atelectasis). In both cases, the lung gets de-aerated. The term non-aerated lung (NAL) is used to refer to both conditions. Subpleural consolidation can be present in any zones. However, the atelectatic consolidation is only visible in the lateral zone (costophrenic view). Consolidated lung is typically visible during pneumonia.

Pleural Effusion

When excess fluid builds up between the lung and the chest cavity, it is called pleural effusion. A trace amount of effusion is normal, particularly in older patients. Effusion builds up below the lung first. Therefore, the lower lateral zones (4 and 8) should be examined to discover trace/medium level of effusions. Pleural effusions will typically not be seen in other zones, unless they are severe. A large effusion is life threatening and should immediately be drained.

Data Collection

Lung imaging is not as standardized as cardiac imaging-both in terms of protocols and quality/quantity of acquisition and in terms of storage, reporting and retrieval/dissemination. For instance, Lung imaging is often used only in emergency settings to examine trauma/chest pain patients and only a few views are acquired. Instead of a complete scan, an exploratory scan is done, and clips are often captured only if obvious pathologies of interest are discovered. Hence, data gathering is challenging. It was even more difficult to label them appropriately and build an ML training pipeline. Because the data was unlabeled, even though there were >300 k clips, only something a subset of clips (with only a few frames per clip labeled) were used in the example model.

Data was acquired from an online repository of ultrasound data comprising data collected by clinicians all over the world, which were anonymized and uploaded to a database containing >500 k clips. However, not all clips were of interest. A physician manually selected clips of potential interest-containing b-lines, effusions, consolidations, covid patients' clips, etc., enabling the grouping of clips of interest together and their dispatch for labeling.

The quality of clips from this source varied widely. As these clips originated from many different institutions and machines, they appeared very diverse in terms of pathologies, patients, etc. However, no explicit labels and reports were associated with any of these data prior to the data being obtained for use in the example model. In terms of probe, the curvilinear probe was the most widely used. In total, 713 clips from the databased were obtained, and 2311 images out of those were used.

Additional data was obtained from a university hospital system (over >300 k DICOMs in total). Not all were lung ultrasound images. Most images were acquired on a Philips Sparq machine, with a phased array probe. Because the phased array isn't the most suitable probe for Lung imaging, the images from this dataset appeared qualitatively very different than the images from the other datasets obtained. Despite this, these images were used in the example model for two reasons: 1) in many clinical situations, the phased array probe for lung imaging is commonly used because they don't have multiple probe types available and/or its time consuming and cumbersome to keep changing probes as well. 2) It increases the diversity of the dataset by adding examples of a very different qualitative nature.

These clips were generally acquired in the emergency department. Since labels weren't available for these images, only a small fraction of these were sampled and used. Overall, ~1300 DICOMs were selected to be obtained from about 900 patients, yielding 3386 images in total.

Data was also collected during a prototype study with two different hospital systems. Although data collection was only a secondary goal of the studies, as the study progressed, more attention was focused on data collection than on the evaluation of the example models described herein. There were 649 clips from one system from 44 patients and 510 clips from the other system from 28 patients. A butterfly probe was used to acquire all these images.

A significant number of these patients have pathologies since the recruitment was focused more on b-lines and consolidation/effusions. Since, the butterfly probe was the target probe, and these images came from well-structured studies with a significant number of pathologies, the use of this dataset was emphasized over other sets in the example model. Images from these studies were oversampled in comparison to data from previous sources. Therefore, the example model was tuned very well to a similar data category acquired using the butterfly probe. The image quality of the upper zones, where low depth was satisfactory, was very good using the butterfly probe. Hence, a-lines, b-lines and pleural-lines were very well visualized.

All studies acquired at the second hospital system also feature clips acquired at very low depth to assess lung sliding/pleural irregularities. These clips were included in the training examples as well, although to a lesser degree. It was noted that these clips bear some resemblance with linear-probe images since linear probes were also used at low-depth.

Data Labeling

Because there were two heads in the example model the labeling was also split up into two categories—a/b/pleural line (A/B) labeling and pleural effusion/consolidation (PE/NAL) labeling. Before finalizing the labeling schemas, a few iterations of labeling with clinical experts were conducted to both fine-tune the tasks being asked for in the labeling exercise, in terms of annotations and classifications, and the guidelines provided to ensure consistent labeling. For a significant number of images, multiple labels per image were also obtained, to be able to track inter-reader agreements.

A example neural network can be implemented for analysis of ultrasound images comprising features of adjacent organs. The various features and layers are built into a single network. The network is multi-headed. The two custom heads function as prediction heads. The two heads group structures and artifacts that appear in the upper zones (anterior, anterolateral zones) together in head 1 and the artifacts from the lower zones (lateral) together in head 2. The idea is that model learns general features until this bifurcation and after that it learns more specific features to the zones that it represents. However, this division is not perfect in all cases: Zones 1-3 and 5-7 can also have effusion and consolidations and zones 4-8 can also feature a-lines, b-lines and pleural-lines, especially when trying to capture the curtain sign. The division isn't strictly necessary but in many cases meant to be helpful to guide the model to learn and group semantically and physiologically similar artifacts/organs together. Therefore, the two heads operate simultaneously when processing images. Downstream algorithms apply rules and post-processing methods to filter and arbitrate between detected features before image annotations are displayed to the user. The multiple outputs of the Zone 1-3, 5-7 heads include features that are used to improve b-line and deaeration detection and analysis. B-lines can also occur in the lower zones, so the methods and systems disclosed herein can operate there also.

For both sets of labeling, image frames from lung clips were displayed but also the video on a side-pane for reference. The labelers were asked to look at the video for context to provide better labels, but ultimately to provide the appropriate labels for the frames they're labeling.

A/B/Pleural Lines' Labeling

For this, the labelers were asked to annotate three items:
1. B-line
2. A-line
3. Pleural-line The annotations for b-lines using straight lines and for a-lines and pleural-lines using free-hand drawings were asked for. And then the following classification questions were asked:
1. Assess the quality of this frame (choose one):
   a. Good
   b. Suboptimal, but clinically acceptable
   c. Poor, clinically unacceptable (select a reason below, then click Submit if you cannot annotate any artifacts/structures)
2. If poor quality, what was the reason (select all that apply)?:
   a. Poor quality image
   b. Not a lung image/clip
   c. Other, please comment below.
3. Assess a score for b-lines: (choose one): 0-10
4. Comments (text box):
5. Is lung sliding absent anywhere in this video (choose one)?
   a. Yes (absent in at least some part of the video)
   b. No (lung sliding is normal)
   c. Not sure
   d. Pleural line not seen in video.

While the initial strategy was asking doctors to do all the annotations and classifications, this was later changed. Sonographers were trained to identify the a-lines, b-lines and pleural-lines patterns. Then the doctors provided b-line scores and answered the question on lung-sliding. If the doctors weren't satisfied with the initial annotations, they were asked to either reject or re-work the annotations. All annotations were therefore reviewed by expert clinicians.

Multiple fine tunings on the instructions through the iterations were conducted. Here were some of the key ones:

For pleural lines, the focus was on trying to get the width of the annotation right—not too thick, not too thin. In later data, a bias towards being a bit thicker was asked for since that'd be easier for the example model to pick up and learn from. Also, the pleura shimmers in the video (unless there's an absence of lung sliding).

For a-lines, the understanding was reinforced that they should be equidistant from the pleural line. Similar to pleural-lines, work was done with them to get the thickness right.

For b-lines, the annotators were asked to annotate only if they go all the way down the screen. They were also asked to look at the video for better context. The b-lines also move with the lung sliding in the video. Consistent movement patterns for other noise artifacts or z-lines aren't observed. Only good and sub-optimal quality frames were used and poor quality ones were discarded for training.

PE/NAL Labeling

For this, the labelers were asked to annotate four items:
1. Consolidation (NAL)
2. Pleural effusion (PE)
3. Diaphragm
4. Spleen/Liver The spleen and liver can be accounted for separately or combined for reduced complexity since the need was only to know that the region was not lung and in fact an abdominal area. Then the following classification questions were also asked:

1. Assess the quality of this still frame (choose one):
   a. Good
   b. Suboptimal, but clinically acceptable
   c. Poor, clinically unacceptable (select a reason below, then click Submit if you cannot annotate any artifacts/structures)
2. If poor quality, what is the reason (select all that apply)?
   a. Poor quality image
   b. Not a lung image/clip
   c. Other (please comment below)
3. Consolidation type:
   a. None
   b. Non-translobar
   c. Translobar
4. Air bronchogram type (use video):
   a. None
   b. Static
   c. Dynamic
5. If pleural effusion is present, what is the type?
   a. None
   b. Simple
   c. Complex
   d. Not Sure
   e. Anechoic
6. Comments (text area)

All the annotations and classifications for these exercises were done by doctors. There were also many fine-tuning steps as the iterations were gone through.

For consolidation and effusion, the focus was on precision rather than sensitivity. If uncertainty was present, the annotators were asked not to annotate. Since effusion is hypoechoic, it could easily be confused with other hypoechoic areas in the image such as rib shadows. So caution while labeling this was encouraged, and only label areas that were certain about were selected.

The idea of consolidation was clarified to include both subpleural consolidations and atelectasis since the visual presentations of these things can be similar. This was termed as non-aerated lung (NAL). The labelers were asked to label any abdominal area beyond the diaphragm as spleen/liver. Even though those areas may contain other structures such as kidney, etc., the broad interest was in non-lung areas beyond the diaphragm and their exact specification was not emphasized in the example model.

Confidence questions were added to the set of classification questions as well. The labelers were asked to add how confident they were in their labels and this information was used to build weights in the loss function. However, it didn't seem like this significantly improved accuracies. Only good and sub-optimal quality frames were used and poor quality ones were discarded for training.

Rib Shadow Labeling

Rib-shadow labels were added much later into the development process. The initial motivation for adding rib-shadow was to improve pleural effusion identification. Often, rib-shadow like hypoechoic areas would get labeled as rib-shadows. Hence, first, rib-shadow was added as another class to the PE/NAL head. However, it turned out that this did not improve pleural effusion prediction accuracy. Therefore, rib-shadows were moved to the A/B/Pleural head since rib-shadows feature more prominently in the upper anterior and anterolateral zones than in the lower zones. Fortuitously, as the development of landmark-based guidance started, having rib-shadow prediction has been crucial in helping to define canonical views for the upper zones.

The labelers were asked to annotate the rib shadow and answer the following questions as well:

1. Is this frame of acceptable diagnostic quality (choose one)?
   a. Yes
   b. No
2. If you segmented rib shadow, how confident are you in your segmentation?
   a. High confidence
   b. Low confidence
   c. No rib shadow present Spine/Curtain Sign Labeling These were added even later than rib-shadows. The primary motivation for these were to support landmark-based guidance for the lower/costophrenic zone. Diaphragms and liver/spleen were already present that helped define the canonical view to some extent. But that was not sufficient to know if the probe was actually adjacent to the lung or not. The curtain sign helped with that. The spine and the spine sign helped ascertain that the probe was being fanned in the right direction towards the spine, as it is done in clinical practice.

The labelers were asked to annotate:
1. Curtain sign
2. Spine
3. Spine sign

In the example model, the spine and the spine sign were combined into a single 'spine' class. If those structures don't exist, the labeler can click the following option: No curtain sign, spine, or spine sign.

Example Model Architecture

Similar to the cardiac models, a core lung model was developed and additional models have been built on top of it. These auxiliary models use features from the core model to predict additional attributes of interest.

However, in contrast to the cardiac model, the core model doesn't predict pose and/or distances. A segmentation model was opted for as the core model instead. The segmentation task was general enough that the core model can learn general features that can then be used in auxiliary models, and be fine-tuned, to specific tasks. Also, when the project started, it wasn't obvious what exactly the product would be. Hence, working on a generic segmentation model and then adding specific auxiliary models on top as the project moved forward, seemed like a good idea (as opposed to working directly on b-line scoring for example).

The example model uses moblinetv3 [1] as its backbone, deeplabv3+[2] as the segmentation layer and some custom layers on top for predictions. These models were lightweight and well-optimized to run on mobile devices, which was an important requirement for target platforms of tablets and mobile devices.

Another key design component was the use of two heads for prediction. Head 1 predicts:

i. A-lines ii. B-lines iii. Pleural-lines iv. Rib-shadows

Head 2 predicts:

I. Diaphragm

II. Liver/spleen

III. Consolidation (NAL)

IV. Pleural Effusion

V. Spine

VI. Curtain sign

The two heads group artifacts that appear in the upper zones (anterior, anterolateral zones) together in head 1 and the artifacts from the lower zones (lateral) together in head 2. The idea was that the example model learns general features until this bifurcation and after that it learns more specific features to the zones that it represents. Zones 1-3 and 5-7 can also have effusion and consolidations and zones 4-8 can also feature a-lines, b-lines and pleural-lines, especially when trying to capture the curtain sign. The division isn't meant to be super strict but is meant to be helpful to guide the example model to learn and group semantically and physiologically similar artifacts/organs together.

The example model was used to do semantic segmentation of a wide range of sizes, frequency and appearance of objects. Pleural lines were rather small but very prevalent. B-lines, liver/spleens, rib-shadows were rather large. Although earlier iterations of the example model (with mobilenetv2 and deeplabv2) struggled with this variation of scale particularly, later models did not have this issue since these problems were largely addressed with the newer state-of-the-art models.

Preprocessing

The images were center cropped and resized. If center-cropping was not appropriate for any image, then a different crop that'd center the US cone area can also be used. This was seen as preferable to a skewed center crop.

Outputs

Model outputs semantic segmentations, that is, every pixel was labeled with the probability of it being assigned to different classes. Two sets of heads give two sets of probabilities. Logits were first obtained, which were softmaxed to achieve probabilities.

For further post-processing, e.g., to display pleural lines, the probabilities were either arg-maxed or thresholded per artifact to achieve a binary mask. Connected component analysis was usually run on these masks to obtain 'blobs' of different artifacts, with one blob representing one contiguous artifact/structure. Various rules and post-processing were applied to these blobs before they get displayed to the users.

Clinical B-Line Scoring

Over the years, two main flavors of model development for b-line scoring were attempted-1) direct (black-box) prediction from an additional shallow neural network head on top of the original network, 2) SVR regression on features derived from the segmentation masks of b-lines, a-lines, pleural-lines, etc.

Although the hope was that the black-box approach would work better, that did not pan out. Having a neural network-based model would also allow the packaging of the core lung model and this auxiliary model into the same TensorFlow graph during deployment. However, the neural network model sometimes produced bizarre results and it was not easy to probe into and figure out what was happening.

The example models using features from segmentation masks were easier to debug and update since it was easy to determine what was happening by observing the segmentation masks. Therefore, the SVR based approach was chosen for improved explainability and ease of debugging.

B-Line Scoring Data Collection

The data for the scoring was collected as part of the annotation exercise itself (described above). B-lines' annotation and scoring were done in the same labeling exercise since the annotations provide context for the scores and vice versa.

For the guidelines on how to score, the following instructions were provided, resulting in a 'hybrid' approach:

1. For distinct B-lines, each line was counted as one.

2. For confluent B-lines, the area of the screen occupied by B-lines was considered as a percentage of the entire screen (taking into account the screen below the pleural line, excluding rib shadows), and divided by 10. For example, 30% of "B-lines hyperechogenicity" corresponds to a score of 3 B-lines.

3. Therefore, the lowest score was 0 and highest was 10, in integer form.

When the b-lines were distinct and clear, they're simply counted as-is by clinicians. They do not use the percentage rule. Hence, they were asked not to change that behavior. However, when there's ambiguity, which was often, they were asked to use the percentage rule. It was to be noted that no measurement devices were used to compute the exact percentages. Rather, this was eyeballed—as is commonly done in clinical practice, and similar to how ejection fraction is often eyeballed by cardiologists. Despite this potential limitation in training data, the example model was able to characterize image features with improved precision.

B-Line Scoring Model

The scoring was done via a support vector regressor (SVR) model. The features used for training also went through a few iterations—first, only the number of b-line pixels after thresholding the probability mask for b-lines was used. Next, additional features were added—number of pleural line pixels, number of a-lines pixels and number of rib-shadow pixels. The idea being b-line scores depend on these other features as well-directly or indirectly. E.g., if there were no pleural lines, then it's unlikely the b-line is genuine. Conversely, if there were too many a-lines, then b-lines should not be present as b-lines and a-lines cannot occur at the same spot. The upper left panel shows a raw image used as input prior to classification. The upper right panel shows a probability mask of B-lines after inference by the model. The lower left panel shows binarization of the image the upper right panel after argmaxing, and the lower right panel shows contiguous structures detected by the model using connected component analysis, which produced two "blobs".

Finally, this feature set was expanded even further. As more attributes of the different landmarks started to be computed, access was gained to many other properties of the segmentation output masks. Hence, those could be leveraged as well, without extra computations.

Connected component analysis was used to group the pixels together. A group of pixels that were connected together were represented as a contiguous structure representing that artifact. These contiguous structures were referred to as 'blobs'. The following attributes were used as features, repeated for each of a-lines, pleural-lines, b-lines and rib-shadows:

1. Total area: The total number of pixels in the binary mask for an artifact.
2. Average area (per 'blob')
3. Maximum area
4. Average of average probability over the blob's mask: a binary mask was constructed for each blob, and then the average probability over that mask was computed. Then the average of those averages was taken.
5. Number of blobs: some very tiny blobs were discarded as noise (less than 20 pixels).
6. Average Major axis length: An ellipse was fitted to each blob. An ellipse has a major axis and a minor axis. This was the average of all the major axis lengths. The idea being contiguous structures/artifacts should have relatively larger major axes.
7. Average Minor axis length: Average minor axis lengths were also added.
8. Average major-minor axis ratio: Since all the artifacts of interest were elongated structure, the blobs should ideally be well fitted with ellipses with larger major axis lengths than minor axis lengths.
9. Average blob centroid x: Each blob's center point's x component was averaged.
10. Average blob centroid y: Each blob's center point's y component was averaged.
11. Average blob centroid angle: Each blob's center point's angle with the cone top was averaged.
12. Average orientation: Each blob's orientation relative to the x-axis was averaged.

As the features were repeated for four artifacts/structures, there were 48 features per image in total. The example model was trained with the input being these 48-dimensional features, and the output being the predicted b-line score, with the training data being the expert provided, percentage-based (hybrid) b-line scores. A linear SVR model was trained, and the best model was chosen by checking the performance on the 'eval' data:

The output of the example model was binned into 3 categories: scores of 0, scores of 1-2 (inclusive) and scores of 3 and above.

The linear weighted kappa for this classification was computed. The example model yielding the best kappa was chosen.

During inference, it was possible that the example model outputs values below 0 and above 10. Since the example model outputs a continuous valued number, this was possible, unlike in classification models where the possibilities were finite. These values were clipped and rounded to output integer scores, with the minimum of 0 and maximum of 10.

Cardiac Landmark Classification

Similar methods to those implemented above are further implemented for classification of cardiac features and/or for features of additional adjacent organs. Annotations or classifications can utilize anatomical features of adjacent organs to determine or assist in determining guidance instructions for imaging of a target organ. For example, an Apical Four Chamber view of the heart should show the apex of the heart, the left and right ventricles, the myocardium, the mitral and tricuspid valves, the left and right atria, and the interatrial septum. As another example, a long axis view of the carotid artery at the bifurcation should show the common, external, and carotid artery and the carotid bulb. In some aspects, image quality is in reference to an image in which a diseased condition, abnormality, or pathology is well visualized. For example, medical images may be labeled by cardiologists, radiologists or other healthcare professionals according to whether they are considered to have a well visualized diseased condition, abnormality, or pathology, and then used to train a machine learning algorithm to differentiate between images based on image quality.

In some aspects, image quality means that some combination of these aforementioned characteristics is present. Effective navigational guidance will need to be provided to ensure the captured ultrasound image satisfies the combination of these image quality characteristics necessary to yield an overall clinical or diagnostic quality image because, in ultrasound imaging, patient presentations can present challenges to obtaining high-resolution, low-noise images. It can be particularly challenging, for example, when trying to evaluate blood flow in the kidney of an obese agent, to get a strong enough blood flow Doppler signal because the kidney is so deep underneath fatty tissue. In a patient who has been a long-term smoker, lung disease can make it very difficult to obtain high quality cardiac images. These conditions are extremely common, and in such situations, image quality can mean an image that may be sub-optimal as far as noise and resolution, but still provides enough information for a diagnosis to be made. In a similar way, patient presentations and pathologies can make it impossible to obtain views that show all the anatomical components of a standard, canonical image. For example, a technically difficult cardiac patient may make it impossible to get an Apical Four Chamber view with all four chambers well defined, but if some images show, say, the left ventricle well, this can be considered a quality image because many critical diagnostic conclusions can be drawn from only that.

In some aspects, the anatomical views used in the present disclosure include one or more of a probe position or window, an imaging plane, and a region or structure being visualized. Examples of probe position or window include parasternal, apical, subcostal, and suprasternal notch. Examples of imaging plane include long-axis (LAX), short-axis (SAX), and four-chamber (4C). Examples of the region or structure being visualized include two-chamber, aortic valve, mitral valve, etc. For example, the anatomical views can include parasternal long-axis (LV inflow/outflow), RV inflow+/−RV outflow, parasternal short-axis (aortic valve level, mitral valve level, papillary muscle level, apical LV level), apical four-chamber, apical five-chamber, apical two-chamber, apical three-chamber, subcostal four-chamber view, subcostal short-axis and long-axis, suprasternal long-axis (aortic arch) and suprasternal short-axis (aortic arch).

Landmark-Based Guidance

Although acquisition of lung ultrasound scans is generally more straightforward and easier to train novices on compared to echocardiography, there is still ample opportunity for machine learning to play a role in enabling novice scanners and ensuring the quality of images obtained by them. In zones of the lung without pathology present, the appropriate positioning of the probe to confirm the absence of pathology was an important part of the overall scanning protocol. Whereas in echocardiography there were specific planes through the heart that represent an ideal or canonical pose for diagnostic purposes for each view, lung ultrasound is more exploratory in nature, and a diagnostic view is more determined by the presence of specific anatomical or artifactual features in the FOV. Moreover, the rich structural information present in cardiac scans that can be used to infer probe pose is not present in all lung zones.

The above fundamental differences between cardiac and lung ultrasound necessitate a fundamentally different approach to guidance for lung ultrasound than for cardiac. Therefore, a novel guidance approach for lung ultrasound, referred to as "landmark-based guidance", was developed. This approach consists of three fundamental features, including:

1. Landmark Detection and Annotation
2. Quality Meter (based on landmark presentation)
3. Auto-Capture Of note, features (2) and (3) are integral parts of a comprehensive ultrasound system, with the goal being to capitalize on the success of these intuitive features for novice cardiac scanning and to streamline the overall experience of changing between guidance systems for different anatomies. However, in the case of lung guidance, the quality meter output was a function of landmark presentation for the zone being imaged, so it only depends on probe position insofar as probe position modifies the landmark presence and location in the FOV. Because different landmarks were visible in different lung zones, the sets of landmarks included in landmark-based guidance have been divided into the following two sets.

Anterior and Upper Lateral Zone Landmark Annotation

As described previously, a canonical image of the healthy lung in these zones (1-3, 5-7 within the 8-zone protocol) should include pleural line, rib shadows, and A-lines. Therefore, post-processing methods to detect and annotate in the image where these landmarks present have been developed. Because each feature represents a different anatomical or artifactual finding, the methods have been refined to address the specific anatomy and physical process associated with imaging the landmark. All landmark detection methods begin with the full output of the softmax layer of the lung segmentation model.

These softmax outputs may be interpreted as class/landmark probabilities since they sum to 1 across each model head, so they will be referred to as landmark probability maps, denoted Plandmark, e.g. $P_{rib}$ for rib shadow class, $P_{pl}$ for pleural line class, and Pal for A-line class. Annotations were generated according to the following landmark-specific methods.

Pleural Line

Annotations for the pleural line were detected by thresholding the example model output followed by a vertical column-based centroid calculation to yield a horizontal line segment for each detected segment of pleural line. This workflow and associated parameters involved in this post-processing workflow are:

1. Threshold the example model output pleural line class probability map (p>0.70).
2. Small blobs (<25 pixels in area) were removed.

3. For each remaining blob, the probability-weighted average depth along each column was computed to derive a horizontal "skeleton" of the pleural line segment.
4. Short pleural line segments (<5 pixels in length) were removed.
5. Both ends of each line segment were cropped by 15% to improve visibility of pleural line in image overlay and remove lower-confidence tips of line segments.

Rib Shadows

Annotations for rib shadows were detected by performing a polar transformation of the example model output and looking for peaks in the projection of this representation onto the angle axis. The specific steps are:

1. The polar transformation of the rib shadow class probability map around the cone center was computed, re-representing the raw map in dimensions of angle and radius (i.e., depth) from cone center.
2. The polar transformed probability map was averaged along the depth axis to create a mean projection of rib shadow probability as a function of angle from cone center.
3. The projection was filtered with a moving average filter of size 7.
4. For ranges along the angle axis where the projection exceeds a pre-determined threshold (p>0.25), the peak within this section of the projection was determined and the rib shadow location was recorded as the angle where this peak occurs.

A-Lines

Annotations for A-lines were detected by projecting the probability map row-wise onto the depth axis and looking for peaks above a given threshold. The specific steps are:

1. The example model output probability map for the A-lines class was projected horizontally onto the depth axis.
2. The projection was filtered with a moving average filter of size 11.
3. For ranges along the depth axis where the projection exceeds a pre-determined threshold (p>0.06), the peak within this section of the projection was determined as the depth of a detected A-line.
4. For each detected A-line, the horizontal location was computed as the weighted average of the probability map column indices within a window of size three around the detected depth (one row below to one row above).

Lower Lateral ("Costophrenic") Zone Landmark Annotation

A canonical image of the healthy lung in the lower lateral zones (4, 8 within the 8-zone protocol) typically includes diaphragm, liver or spleen, spine, and intermittent curtain sign (dependent on respiratory phase). Similar to the approach for upper zones, landmark-specific post-processing strategies have been developed to detect and localize each of these landmarks. Annotations were generated according to the following methods:

Diaphragm

Annotation of the diaphragm follows a similar approach to the pleural line method, except that the projection was performed along the horizontal axis. Diaphragm was detected by thresholding the example model output probability map for diaphragm class, followed by a horizontal row-wise centroid calculation to yield a vertical line segment centered on the diaphragm. The specific steps and associated parameters involved in this post-processing workflow are:

1. Threshold the example model output diaphragm class probability map (p>0.40).
2. For the largest single blob above threshold, compute the probability-weighted average depth along each row to derive a vertical "skeleton" line centered over diaphragm. 30
3. Remove short pleural line segments (<3 pixels in length).
4. Crop both ends of each line segment by 15% to improve visibility of pleural line in image overlay and remove lower-confidence tips of line segments.

Spine

The spine was detected based on simple thresholding of the example model output followed by centroid calculation of the largest thresholded blob. The specific steps are:

1. The probability map for spine was thresholded (p>0.60) to identify candidate blobs
2. The centroid of the single largest blob was used as the annotation location Liver/Spleen The liver and spleen were combined into a single output class in the lower lateral zone model head. Different strategies for annotating liver/spleen were experimented with, and it was found that the centroid-based method used for spine above was not stable over time, giving a jittery impression to the annotations. Thus, a method similar to the rib shadow approach outlined above was implemented to determine the angle at which liver or spleen were most prominent, and then draw the label at a fixed depth at this angle in the image. The specific steps are:

1. Compute the polar transformation of the liver/spleen class probability map, re-representing the map in dimensions of angle and radius from cone center.
2. Average the polar transformed probability map along the depth axis to create a mean projection of liver/spleen probability as a function of angle from cone center.
3. Filter the projection with a moving average filter of size 7.
4. For ranges along the angle axis where the projection exceeds a pre-determined threshold (p>0.30), the peak within this section of the projection was determined and the liver/spleen location was recorded as the angle where this peak occurs.
5. The annotation was drawn as text overlay on the image at the detected angle and a fixed depth.

Curtain Sign

The curtain sign was an artifact resulting from the obscuring of signal distal to the pleural line in lower lateral zones that appears as the subject inhales and the pleural line appears in the top left of the FOV. Because of the nature of the curtain as an artifact where signal was obscured beyond a shallow structure, the same methods as for rib shadows were used where a polar transformation of the example model output was performed and peaks in the projection of this representation onto the angle axis were sought. The specific steps are:

1. The polar transformation of the curtain sign class probability map was computed, re-representing the map in dimensions of angle and radius from cone center.
2. The polar transformed probability map was averaged along the depth axis to create a mean projection of curtain probability as a function of angle from cone center.
3. The projection was filtered with a moving average filter of size 7.

4. For ranges along the angle axis where the projection exceeds a pre-determined threshold (p>0.30), the peak within this section of the projection was determined and the curtain location was recorded as the angle where this peak occurs.
5. The annotation was drawn as text overlay on image at the detected angle and a fixed depth.

Quality Meter

The Quality Meter (QM) is an important feature for a comprehensive ultrasound imaging system, such as those described herein. The benefit of the QM is that it gives real-time user feedback on image quality as a function of probe position, which provides an intuitive way for users to work toward an appropriate probe position and associated image via slow, controlled probe manipulations. Therefore, the development of a QM for lung ultrasound guidance that replicates the basic functionality of the cardiac QM and provides a similar intuitive user experience was sought. The basic requirements of the QM include:

1. The QM responds smoothly to perturbations in probe position, such that small movements produce incremental changes in the QM value.
2. There is a target threshold value above which images were deemed to be of sufficient quality for diagnostic purposes. The threshold of 70% is used here to be consistent with the cardiac guidance product.
3. For lung guidance, image quality may be assumed to reflect both the presence and quality of individual landmarks that were typically present in canonical images of healthy lungs. Different landmarks may contribute with different weights to the aggregate QM score, reflecting their distinct relative importance to diagnostic quality.

With the above requirements as guiding principles, a system to estimate an aggregate image quality score from individual landmark scores and weights was developed. The fundamental idea behind this approach is to determine the specific, measurable aspects of each landmark that: (a) give rise to a subjective concept of "quality" for that landmark; and (b) can be modulated by manipulating probe position. The overall image quality then becomes a sum of the individual landmark scores, weighted by their relative importance.

Zone-Specific Landmark-Based Quality Meter

For each set of zones, the aggregate image quality (IQ) was assumed to be a sum of the individual landmark scores. The landmark weights were used to provide a stronger influence on the quality score for landmarks that were more critical to the diagnostic usefulness of the images. For example, the pleural line was critical to upper zone lung images, whereas A-lines were not strictly necessary for diagnostic utility.

The landmark quality scores for each landmark were defined as mathematical functions of landmark properties that were thought to be important for the subjective quality of each landmark. The specific set of properties used varies by landmark, but all were computed by initially performing an argmax operation on the example model output for each head to determine the most likely output class on a pixel-level basis. For each landmark, a connected components algorithm was used to distinguish separate structures in the argmax output, and a comprehensive set of morphometric properties was computed for each structure. Each landmark was scored based on a subset of this list thought to be most relevant to that specific landmark. An example implementation of a user interface containing a landmark identification and, scoring, and pathology indicators was implemented.

Landmark Quality Score Functions

Mathematical functions for calculating a landmark quality score based on values of the landmark features were defined based on knowledge of specific location, size, and orientation characteristics described as important to the presentation of the landmark by experts in the field. The overall quality score equation for each landmark was calculated as the product for a combination of individual features specific to that landmark.

Landmark Quality Score Parameter Values

The parameter values in the landmark scoring functions above were adjusted by conducting an initial analysis of the distributions of the values of each feature across a broad spectrum of image qualities. Initial values were selected to calibrate the exponential functions to function effectively over the observed ranges of values. The final tuning was achieved through conducting a survey of 500 clips from each set of zones to determine the suitability of each clip for autocapture based on apparent diagnostic usefulness. The parameters were then carefully adjusted to increase the probability that an aggregate quality meter score exceeding a 70% threshold would deliver an image of sufficient diagnostic quality, thereby enabling autocapture according to the criteria outlined in the aforementioned section.

Quality Score Calculation

The quality meter score was derived from the summation of individual landmark scores, wherein two sets of landmarks were specific to each lung zone set. For upper anterior and lateral zones (1-3, 5-7), scores of the pleural line, A-lines, and rib shadow predictions from the example model were calculated individually before being combined to derive an aggregate quality score. Conversely, for lower lateral zones (4, 8), predictions of the diaphragm, liver/spleen, spine, and curtain sign were utilized. Each individual landmark quality score was an exponential mathematical function of particular morphometric characteristics 36 that characterize the sets of voxels identified by the example model as belonging to a specific landmark's class. In the scoring of the pleural line, for instance, all contiguous areas of the image identified by the example model as the pleural line were examined, with metrics such as area, average model output probability, length, 2D location, and angle being calculated. These metrics were applied to score the pleural line and the other landmarks, respectively. Lastly, the individual landmarks were weighted according to their relative importance to diagnostic image quality, and their scores were summed to provide the total quality score. The parameters characterizing individual landmarks and landmark weights were adjusted with an aim of a 70% image quality score being the desirable threshold for a diagnostic quality image, aligning with the cardiac guidance product.

AutoCapture and Save Best Clip Features

The autocapture feature monitors the quality meter as the user zeroes in on an image of suitable diagnostic quality, and automatically starts capturing a clip of a fixed duration once a certain threshold has been achieved and sustained for a pre-determined time span. The software also consistently monitors the retrospective best fixed duration viewed during the session and reserves the frame set corresponding to that time duration in a buffer. If the user was unable to produce an image surpassing the autocapture threshold, they have the option to utilize the Save Best Clip (SBC) feature to save the highest quality clip encountered instead of an autocaptured clip. These features function to deliver an intuitive user experience.

While preferred aspects of the present invention have been shown and described herein, it will be obvious to those skilled in the art that such aspects are provided by way of example only. It is not intended that the invention be limited by the specific examples provided within the specification. While the invention has been described with reference to the aforementioned specification, the descriptions and illustrations of the aspects herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the aspects of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. An ultrasound imaging system configured for conducting a diagnostic procedure on a subject, the ultrasound imaging system comprising:

an ultrasound imaging probe;

a computing system; and a computer-readable storage medium, storing instructions that, when executed by a processor of the computing system cause the ultrasound imaging system to:

receive a selection of the diagnostic procedure for imaging a target organ of the subject;

acquire a plurality of ultrasound images comprising one or more features of an imaged organ of the subject using the ultrasound imaging probe;

process the plurality of ultrasound images using a machine learning model to automatically determine that the one or more features of the imaged organ comprise features corresponding to features of an adjacent organ of the subject;

determine based at least in part on the features corresponding to the adjacent organ, one or more probe placement instructions expected to produce an improvement in a quality of a subsequently acquired ultrasound image of the target organ; and provide a user of the ultrasound imaging system with the one or more probe placement instructions, wherein providing the one or more probe placement instructions comprises determining that a plurality of imaging landmarks are present in the plurality of acquired ultrasound images; and computing the one or more probe placement instructions based at least in part on the plurality of imaging landmarks, wherein the computing system is configured to identify that one or more of the plurality of imaging landmarks correspond to features that are not comprised in the target organ, and wherein the plurality of imaging landmarks comprise anatomical landmarks of the target organ and anatomical landmarks of the adjacent organ.

2. The ultrasound imaging system of claim 1, wherein the imaged organ is a lung of the subject and the adjacent organ is a diaphragm of the subject; or wherein the imaged organ is the diaphragm of the subject and the adjacent organ is the lung of the subject.

3. The ultrasound imaging system of claim 1, wherein the one or more probe placement instructions comprise instructions to adjust a landing spot of the ultrasound imaging probe.

4. The ultrasound imaging system of claim 1, wherein the plurality of imaging landmarks comprises: lung imaging landmarks selected from the group of: pleural lines, A-lines, B-lines and rib shadows; or cardiac imaging landmarks selected from the group of: a parasternal long axis view, a parasternal short axis view, an apical two, three, four or five chamber view, and a subcostal view.

5. The ultrasound imaging system of claim 1, wherein the computing system is further configured to acquire a subsequent plurality of ultrasound images of the target organ, and identify a subset of the subsequently acquired plurality of ultrasound images which meet a minimum quality threshold and/or minimum length threshold; and automatically save the subset of the subsequently acquired ultrasound images in a memory of the ultrasound imaging system.

6. The ultrasound imaging system of claim 1, wherein one or more of the plurality of imaging landmarks is annotated and displayed to a user.

7. The ultrasound imaging system of claim 1, wherein the one or more probe placement instructions comprise a plurality of probe placement instructions and are displayed to the user through a graphical user interface of the ultrasound imaging system.

8. The ultrasound imaging system of claim 1, wherein the imaged organ is a heart of the subject and the target organ is a lung of the subject; or wherein the imaged organ is the lung of the subject and the target organ is the heart of the subject.

9. The ultrasound imaging system of claim 8, wherein the diagnostic procedure comprises a lung imaging procedure.

10. The ultrasound imaging system of claim 9, wherein the computing system is further configured to automatically identify one or more lung zones from comprised in the acquired plurality of ultrasound images.

11. The ultrasound imaging system of claim 10, wherein the automatic identification comprises an identification that a visible lung zone of the one or more lung zones comprised in the acquired plurality of ultrasound images is different from a target lung zone of the diagnostic procedure.

12. The ultrasound imaging system of claim 11, wherein the one or more probe placement instructions comprise instructions to adjust the ultrasound imaging probe to a probe placement expected to produce subsequent images of the target lung zone of the diagnostic procedure.

13. The ultrasound imaging system of claim 12, wherein the one or more probe placement instructions comprise instructions to slide the ultrasound imaging probe in a direction expected to point a transducer of the probe toward the target lung zone of the diagnostic procedure.

14. The ultrasound imaging system of claim 1, wherein the diagnostic procedure comprises a sequential evaluation of a plurality of organs.

15. The ultrasound imaging system of claim 14, wherein the plurality of organs comprise a heart of the subject and one or more lungs of the subject.

16. A method for guiding an ultrasound imaging procedure, the method comprising:

selecting a diagnostic procedure for imaging a target organ of a subject using an ultrasound imaging probe of an ultrasound imaging system;

acquiring a plurality of ultrasound images comprising one or more features of an imaged organ of the subject using the ultrasound imaging probe;

processing the plurality of ultrasound images using a machine learning model to automatically determine that the one or more features of the imaged organ comprise features corresponding to features of an adjacent organ of the subject;

computing based at least in part on the features corresponding to the adjacent organ, one or more probe placement instructions expected to produce an improvement in a quality of a subsequently acquired ultrasound image of the target organ; and providing a user of the ultrasound imaging system with the one or more probe placement instructions, wherein providing the one or more probe placement instructions comprises determining that a plurality of imaging landmarks are present in the plurality of acquired ultrasound images; and computing the one or more probe placement instructions based at least in part on the plurality of imaging landmarks, wherein the method further comprises identifying that one or more of the plurality of imaging landmarks correspond to features that are not comprised in the target organ, and wherein the plurality of imaging landmarks comprise anatomical landmarks of the target organ and anatomical landmarks of the adjacent organ.

17. A non-transitory computer-readable medium, storing instructions that, when executed by a processor of a computer, cause the computer to:

receive a selection of a diagnostic procedure for imaging a target organ of a subject;

acquire a plurality of ultrasound images comprising one or more features of an imaged organ of the subject using an ultrasound imaging probe of an ultrasound imaging system;

process the plurality of ultrasound images to automatically determine that the one or more features of the imaged organ comprise features corresponding to features of an adjacent organ of the subject;

determine based at least in part on the features corresponding to the adjacent organ, one or more probe placement instructions expected to produce an improvement in a quality of a subsequently acquired ultrasound image of the target organ; and provide a user of the ultrasound imaging system with the one or more probe placement instructions, wherein providing the one or more probe placement instructions comprises determining that a plurality of imaging landmarks are present in the plurality of acquired ultrasound images;

and computing the one or more probe placement instructions based at least in part on the plurality of imaging landmarks, wherein the instructions further cause the processor to identify that one or more of the plurality of imaging landmarks correspond to features that are not comprised in the target organ, and wherein the plurality of imaging landmarks comprise anatomical landmarks of the target organ and anatomical landmarks of the adjacent organ.

\* \* \* \* \*